US012708480B2

(12) United States Patent
Kreider et al.

(10) Patent No.: US 12,708,480 B2
(45) Date of Patent: Aug. 18, 2026

(54) BIOPSY SITE MARKER FOR LIMITED MIGRATION

(71) Applicant: Devicor Medical Products, Inc., Cincinnati, OH (US)

(72) Inventors: Elijah Kreider, Liberty Township, OH (US); Peter Shadix, Cincinnati, OH (US); Emmanuel V. Tanghal, Mason, OH (US); Jordan Rebellino, Cincinnati, OH (US); Andrew Small, Galena, OH (US); Ramon Alberto Ramos, Loveland, OH (US); Taylor Vohland, West Chester, OH (US); Jack A. Randall, Cincinnati, OH (US); David C. McBreen, Cincinnati, OH (US); LeRonda Perry, Elkridge, MD (US); Edward A. Rhad, Fairfield, OH (US); Jessica P. Leimbach, Cincinnati, OH (US); Sarah Payne, Cincinnati, OH (US); Anne E. Storer, Cincinnati, OH (US); Andrew T. Robinson, Fort Collins, CO (US); John Kevin Bruce, Morrow, OH (US); Rachel Yoon Choung, Studio City, CA (US)

(73) Assignee: Devicor Medical Products, Inc., Cincinnati, OH (US)

( * ) Notice: Subject to any disclaimer, the term of this patent is extended or adjusted under 35 U.S.C. 154(b) by 0 days.

(21) Appl. No.: 18/653,209

(22) Filed: May 2, 2024

(65) Prior Publication Data

US 2024/0277447 A1 Aug. 22, 2024

Related U.S. Application Data

(63) Continuation of application No. 17/528,666, filed on Nov. 17, 2021, now Pat. No. 12,004,911, which is a (Continued)

(51) Int. Cl.
*A61B 90/00* (2016.01)

(52) U.S. Cl.
CPC ...... *A61B 90/39* (2016.02); *A61B 2090/3908* (2016.02); *A61B 2090/3925* (2016.02);

(Continued)

(58) Field of Classification Search
CPC .............. A61B 90/39; A61B 2090/3904–3995
See application file for complete search history.

(56) References Cited

U.S. PATENT DOCUMENTS

| | | | |
|---|---|---|---|
| 6,083,524 | A | 7/2000 | Sawhney et al. |
| 6,162,241 | A | 12/2000 | Coury et al. |

(Continued)

FOREIGN PATENT DOCUMENTS

| | | | | |
|---|---|---|---|---|
| CN | 1672630 A | 9/2005 | | |
| CN | 104540447 A | 4/2015 | | |
| WO | WO-2016073912 A1 * | 5/2016 | ............. | A61B 10/02 |

OTHER PUBLICATIONS

Sakamoto et al. Evaluation of the dislocation and long-term sonographic detectability of a hydrogel-based breast biopsy site marker. Breast Cancer. 25, 575â582 (2018). doi: 10.1007/s12282-018-0854-8. (Year: 2018).*

(Continued)

*Primary Examiner* — Anh Tuan T Nguyen
*Assistant Examiner* — Younhee Choi
(74) *Attorney, Agent, or Firm* — FBT Gibbons LLP

(57) ABSTRACT

A biopsy site marker includes a carrier and a marker element. The marker element is disposed within the carrier. The carrier including a first marker material and a second marker material. The first marker material and the second marker material are each configured to expand in the pres- (Continued)

ence of moisture. The first marker material is configured to expand at a rapid rate relative to the second marker material in the presence of moisture.

19 Claims, 19 Drawing Sheets

Related U.S. Application Data continuation of application No. PCT/US2020/035190, filed on May 29, 2020.

(60) Provisional application No. 62/854,352, filed on May 30, 2019.

(52) U.S. Cl.
CPC ................ *A61B 2090/3966* (2016.02); *A61B 2090/3987* (2016.02)

(56) References Cited

U.S. PATENT DOCUMENTS 6,270,464 B1 8/2001 Fulton, III et al.
6,356,782 B1 3/2002 Sirimanne et al.
6,605,294 B2 8/2003 Sawhney
8,600,481 B2 12/2013 Sirimanne et al.
8,939,910 B2 1/2015 Fisher
9,220,588 B2 12/2015 Shinar et al.
9,669,113 B1 * 6/2017 Sirimanne .............. A61B 90/39
2004/0030262 A1 * 2/2004 Fisher .................... A61B 90/39 600/564
2010/0030106 A1 2/2010 Weizman
2013/0226026 A1 * 8/2013 Dillard .................. A61B 10/02 604/174
2014/0046347 A1 * 2/2014 Cully ..................... A61B 17/11 606/151
2016/0354178 A1 12/2016 Mayes et al.
2016/0374774 A1 12/2016 Fisher
2017/0231716 A1 * 8/2017 Ahari ..................... A61B 10/02 600/431
2018/0289444 A1 10/2018 Blair et al.

OTHER PUBLICATIONS

Eby et al. Preoperative and intraoperative sonographic visibility of collagen-based breast biopsy marker clips. Acad Radiol. 17(3):340-7 (2010). doi: 10.1016/j.acra.2009.10.017. Epub Dec. 30, 2009. (Year: 2009).*

International Search Report and Written Opinion dated Nov. 2, 2020 for Application No. PCT/US2020/035190, 14 pages.

Chinese Office Action dated Jun. 27, 2023 for Application No. 202080038694.1, 16 pages.

Extended European Search Report dated Jan. 22, 2024 for Application No. 23201822.6, 3 pages.

* cited by examiner 122
12

30
122
12

120
12
122
10
30
100

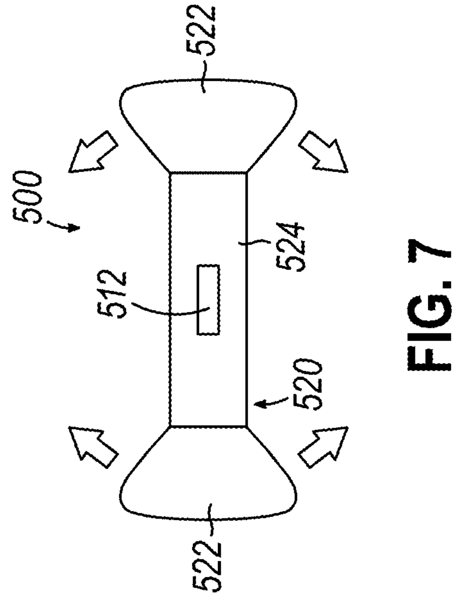
FIG. 7
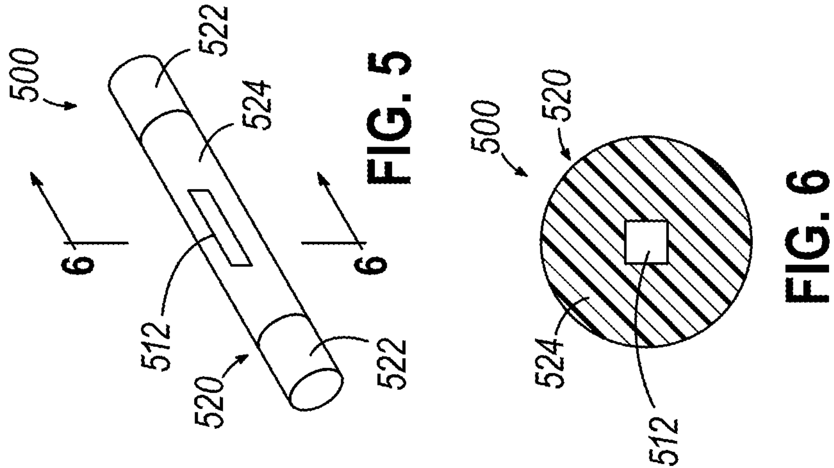
FIG. 5
FIG. 6

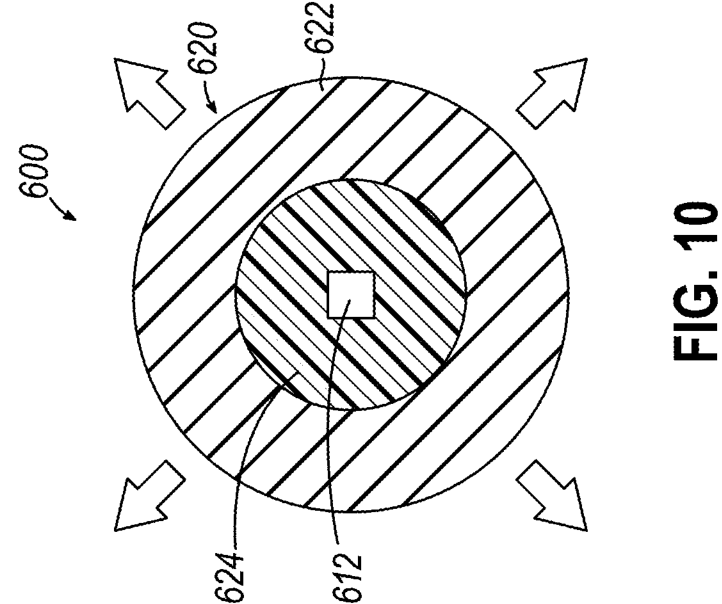
FIG. 10
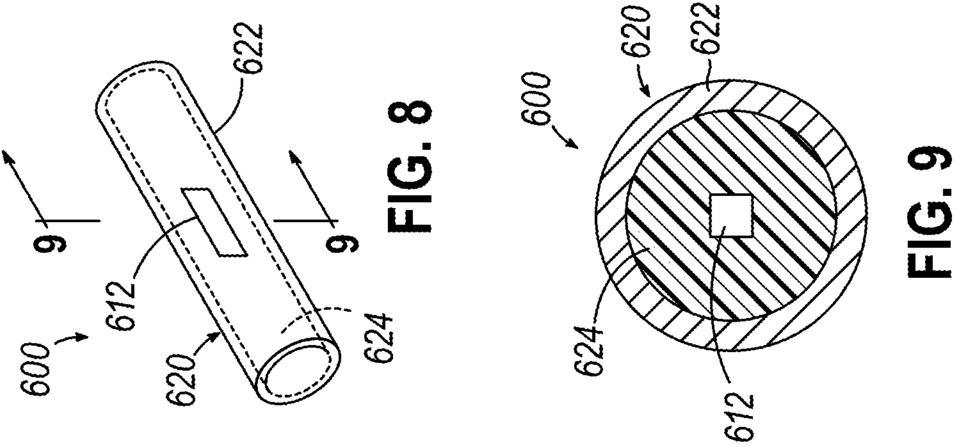
FIG. 8
FIG. 9

700
730
730
722
712
740
720
730
722
730

700
730
722
712
740
730
722

700
720
740
724
712

800
812
824
820
822

800
812
824
820
822
822

800
812
824
820
822
822

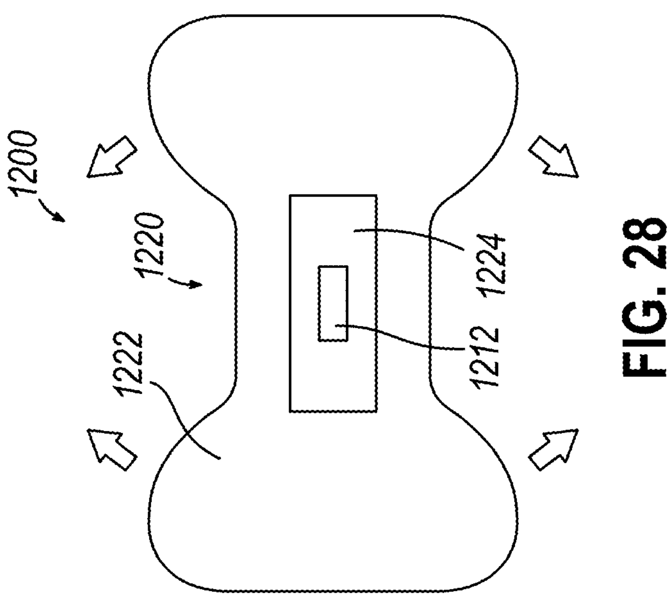
FIG. 28
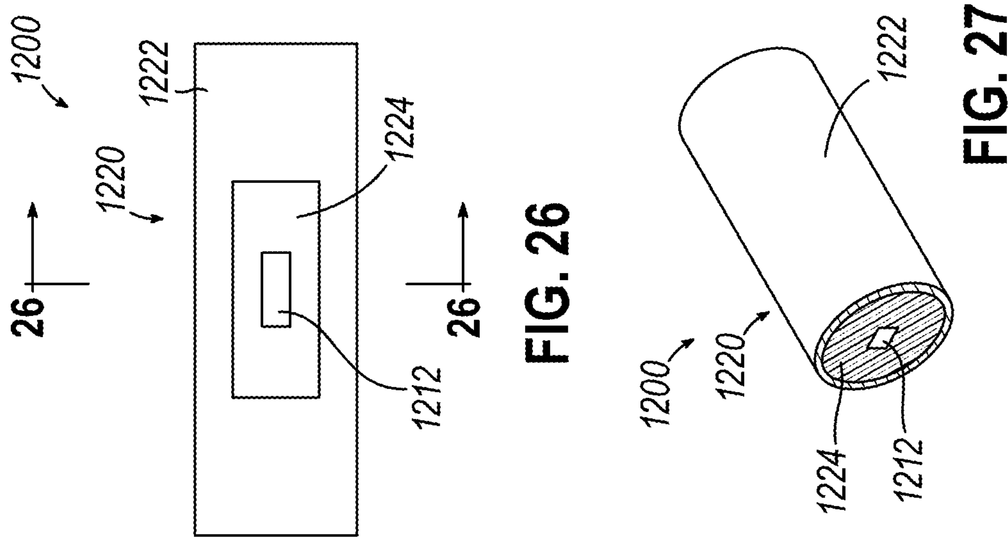
FIG. 26
FIG. 27

BIOPSY SITE MARKER FOR LIMITED MIGRATION

PRIORITY

This application is a continuation of U.S. Ser. No. 17/528,666, entitled "Biopsy Site Marker for Limited Migration," filed on Nov. 17, 2021, which is a continuation of International Application Number PCT/US2020/035190 entitled "Biopsy Site Marker for Limited Migration," filed on May 29, 2020, which claims priority to U.S. Provisional Application Ser. No. 62/854,352 entitled "Biopsy Site Marker for Limited Migration," filed on May 30, 2019, the disclosures of which are incorporated by reference herein.

BACKGROUND

A number of patients will have breast biopsies because of irregular mammograms and palpable abnormalities. Biopsies can include surgical excisional biopsies and stereotactic and ultrasound guided needle breast biopsies. In the case of image directed biopsy, the radiologist or other physician may take a small sample of the irregular tissue for laboratory analysis. If the biopsy proves to be malignant, additional surgery (e.g., a lumpectomy or a mastectomy) may be required. In the case of needle biopsies, the patient may return to the radiologist a day or more later, and the biopsy site (the site of the lesion) may need to be relocated in preparation for the surgery. An imaging system, such as ultrasound, magnetic resonance imaging (MRI) or x-ray may be used to locate the biopsy site. In order to assist the relocation of the biopsy site, a marker may be placed at the time of the biopsy.

The use of markers used after breast biopsies to mark the location where the biopsied tissue was removed is described in the following US patents: U.S. Pat. No. 6,083,524, "Polymerizable biodegradable polymers including carbonate or dioxanone linkages," issued Jul. 4, 2000; U.S. Pat. No. 6,162,241, "Hemostatic tissue sealants," issued Dec. 4, 2000; U.S. Pat. No. 6,270,464, "Biopsy localization method and device," issued Aug. 7, 2001; U.S. Pat. No. 6,356,782, "Subcutaneous cavity marking device and method," issued Mar. 12, 2002; U.S. Pat. No. 6,605,294, "Methods of using in situ hydration of hydrogel articles for sealing or augmentation of tissue or vessels," issued Aug. 12, 2003; U.S. Pat. No. 8,600,481, "Subcutaneous cavity marking device," issued Dec. 3, 2013 and U.S. Pat. No. 8,939,910, "Method for enhancing ultrasound visibility of hyperechoic materials", issued Jan. 27, 2015. All of these US patents are incorporated by reference in their entirety.

Once a marker is placed at a biopsy site, the marker can later be relocated to identify the biopsy site in subsequent follow-up procedures. In some contexts, a placed marker may not completely correspond to the biopsy site. For instance, the marker may migrate from the biopsy site to another nearby location during the intervening time between the biopsy procedure and subsequent follow-up procedures. This could lead to difficulties with identifying the biopsy site during subsequent follow-up procedures. Accordingly, it may be desirable to incorporate features into a marker to maintain the marker in a fixed position over time.

While several systems and methods have been made and used for obtaining a biopsy sample and marking a biopsy site, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

FIG. 5 depicts a perspective view of another exemplary biopsy site marker;

FIG. 6 depicts a cross-sectional view of the marker of FIG. 5, the cross-section taken along line 6-6 of FIG. 6;

FIG. 7 depicts a side elevational view of the marker of FIG. 5, with the marker in an initially hydrated state;

FIG. 8 depicts a perspective view of yet another exemplary biopsy site marker;

FIG. 9 depicts a cross-sectional view of the marker of FIG. 8, with the cross-section taken along line 9-9 of FIG. 8;

FIG. 10 depicts another cross-sectional view of the marker of FIG. 8, with the marker in an initially hydrated state;

FIG. 26 depicts a side elevational view of still another exemplary biopsy site marker;

FIG. 27 depicts a perspective cross-sectional view of the marker of FIG. 26, with the cross-section taken along line 26-26 of FIG. 26;

FIG. 28 depicts another side elevational view of the marker of FIG. 26, with the marker in an initially hydrated state;

Figures 1A, 1B, 1C:
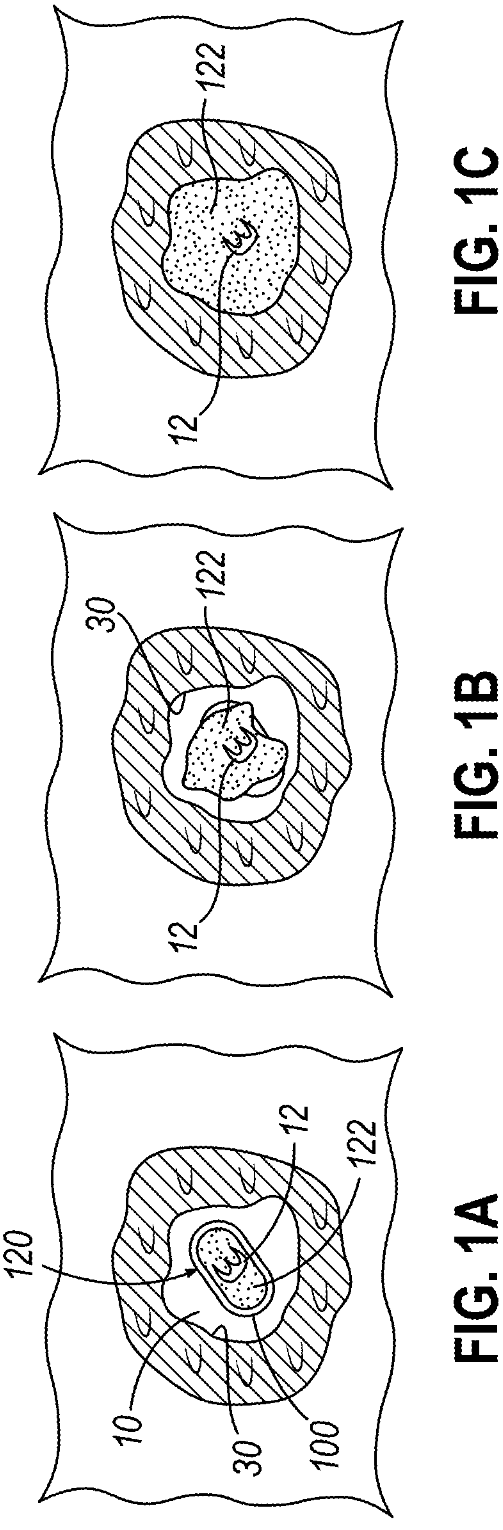
FIGS. 1A, 1B, and 1C show exemplary aspects of placement of a biopsy site marker, in accordance with aspects of the present disclosure.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It may be beneficial to be able to mark the location or margins of a lesion, whether temporarily or permanently, prior to or immediately after removing or sampling it. Marking prior to removal may help to ensure that the entire lesion is excised, if desired. Alternatively, if the lesion were inadvertently removed in its entirety, marking the biopsy site immediately after the procedure would enable reestablishment of its location for future identification.

Once a marker is positioned at a biopsy site, it may be desirable for the marker to remain visible under ultrasound. It may also be desirable to make the marker readily identifiable relative to other structural features of a patient. For instance, it may be desirable for the marker to be distinguishable under ultrasound visualization from microcalcifications to avoid inadvertently characterizing the marker as a microcalcification during subsequent ultrasonic examinations. Generally, microcalcifications are used in the field to identify suspicious lesions or masses. Thus, it is generally desirable for the ultrasound view to be distinguishable as a marker and not inadvertently identified as a new mass.

I. EXEMPLARY MARKER

Aspects presented herein relate to devices and procedures for manufacturing a marker for percutaneously marking a biopsy cavity (10) having surrounding tissue (30), as shown in FIGS. 1A-1C. For instance, as seen in FIG. 1A, a marker (100) may be initially placed in the biopsy cavity (10) to facilitate relocation of the biopsy site. Marker (100) may comprise a carrier (120) and a marker element (12). Carrier (120) generally includes a bioabsorbable marker material (122). Thus, carrier (120) is generally configured for absorption into a patient after placement of marker (100) within the biopsy cavity (10). In some examples, carrier (120) can include a plurality of microbubbles to enhance visualization of carrier (120) under ultrasound. As will be described in greater detail below, marker material (122) is generally bioabsorbable such that marker material (122) may be generally absorbed into the patient's tissue over time. In the present example, marker material (122) comprises a hydrogel that is initially in a dehydrated state. Although a hydrogel is used in the present example, it should be understood that in other examples marker material (122) may comprise other known bioabsorbable materials In the present example, marker (100) further includes a marker element (12) that is generally not bioabsorbable. Marker element (12) may comprise a radiopaque or echogenic marker embedded within the bioabsorbable marker material (122) of carrier (120). For instance, marker element (12) may comprise metal, hard plastic, or other radiopaque or hyperechoic materials known to those of ordinary skill in the art in view of the teachings herein. In other examples, marker (100) may be formed without a marker element (12). In still other examples, marker (100) may be formed with only marker element (12) such that carrier (120) is omitted and marker element (12) is in a "bare" form. In other words, in some examples, marker (100) is formed of only carrier (120) as a bare clip.

Marker material (122) is generally expandable once disposed within a patient at a biopsy site. As shown in FIGS. 1B and 1C, the initially dehydrated marker material (122) may absorb fluid from the surrounding tissue (30) into which it is inserted. In response to this absorption of fluid, marker material (122) may swell, thereby permitting carrier (120) to fill a cavity formed at a biopsy site by removal of tissue samples during a biopsy procedure. Biodegradable materials may be particularly suitable in applications where it is desired that natural tissue growth be permitted to completely or partially replace the implanted material over time. Accordingly, biocompatibility is ensured, and the natural mechanical parameters of the tissue are substantially restored to those of the pre-damaged condition.

Marker (100) may be inserted into the body either surgically via an opening in the body cavity (30), or through a minimally invasive procedure using such devices as a catheter, introducer or similar type insertion device. Marker (100) may be delivered immediately after removal of the tissue specimen using the same device used to remove the tissue specimen itself. Follow-up noninvasive detection techniques, such as x-ray mammography or ultrasound may then be used by the physician to identify, locate, and monitor the biopsy cavity site over a period of time via marker (100).

Marker (100) of the present example is large enough to be readily visible to a clinician under x-ray or ultrasonic viewing, for example; yet small enough to be able to be percutaneously deployed into the biopsy cavity and to not cause any difficulties with the patient. Although examples are described in connection with treatment and diagnosis of breast tissue, aspects presented herein may be used for markers in any internal, tissue, e.g., in breast tissue, lung tissue, prostate tissue, lymph gland tissue, etc.

The hydration of the marker material (122) of carrier (120) by the natural moisture of the tissue surrounding it causes expansion of the polymer and thus minimizes the risk of migration. The growing hydrogel-based marker material (122) centers marker (100) in the biopsy cavity as it grows. As the hydrogel expands, naturally present moisture from the surrounding tissue, the hydration enables increasing sound through transmission, appears more and more hypoechoic and is easy to visualize on follow up ultrasound studies.

The hydrated hydrogel marker material (122) of carrier (120) may also be used to frame permanent marker (12). The hypoechoic nature of the hydrated marker material (122) enables ultrasound visibility of the permanent marker (12) within the hydrogel hydrated marker material (122) because the permanent marker (12) is outlined as a specular reflector within a hypoechoic hydrated marker having a water-like nonreflective substrate.

II. EXEMPLARY MARKER DELIVERY DEVICE

Figure 2:
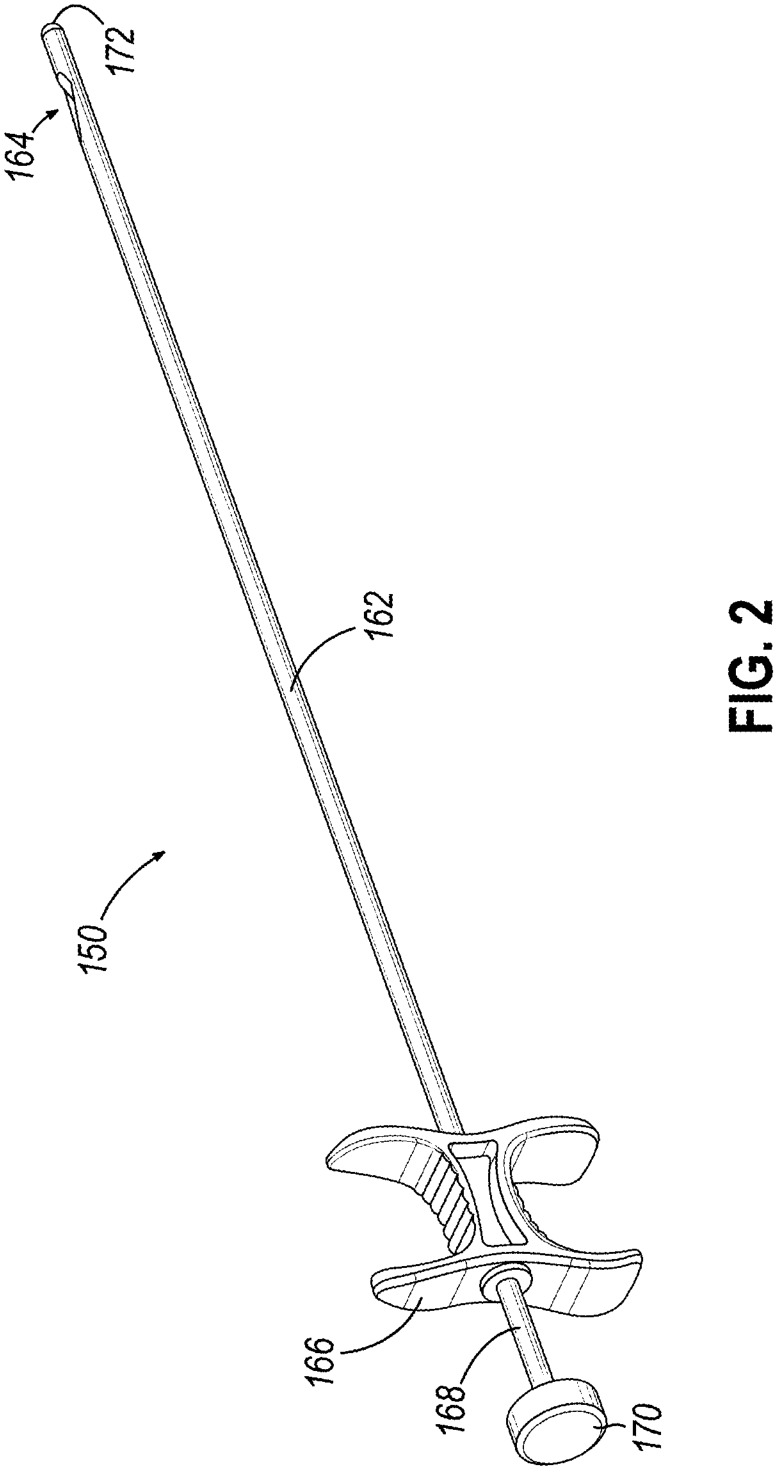
FIG. 2 depicts a perspective view of an exemplary marker delivery device.

In some examples, it may be desirable to deploy marker (100) described above within the body cavity (30) using certain marker delivery devices. For instance, FIGS. 2 and 3 show an exemplary marker delivery device (150) which includes an elongate outer cannula (162) having a marker exit, such as side opening (164) formed adjacent to, but spaced proximally from, the distal end of the cannula (162).

A grip (166) can be provided at the proximal end of cannula (162). A push rod (168) can be provided, with push rod (168) extending coaxially in cannula (162) such that push rod (168) is configured to translate within cannula (162) to displace one or more markers through side opening (164) (see FIG. 3). Rod (168) may have sufficient rigidity in compression to push a marker from an internal lumen (165) of cannula (162) out through opening (164) yet be relatively flexible in bending. A plunger (170) is coupled at the proximal end of rod (168) for forcing rod (168) distally in cannula (162) to deploy a marker out of cannula (162).

A user may grasp grip (166) with two fingers and may push on plunger (170) using the thumb on the same hand, so that marker delivery device (160) is operated by a user's single hand. A spring (not shown) or other feature may be provided about rod (168) to bias rod (168) proximally relative to grip (166) and cannula (162).

Figure 3:
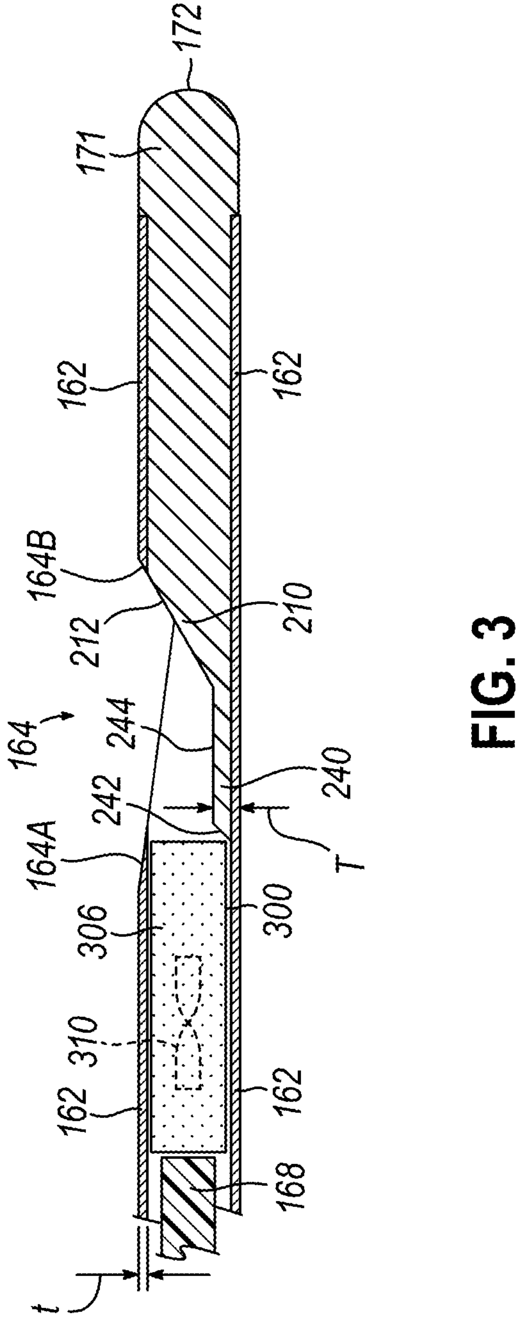
FIG. 3 depicts a side cross-sectional view of the marker delivery device of FIG. 2.

FIG. 3 shows a cross-sectional view of a distal portion of the marker delivery device (160). As can be seen, a biopsy marker (300) similar to marker (100) described above is disposed within internal lumen (165) of cannula (162). In the present example, marker (300) comprise a biodegradable or otherwise resorbable marker material (306), such as a generally cylindrically shaped body of collagen, hydrogel, or etc., and a metallic, generally radiopaque permanent marker or marker element (310) (shown in phantom) disposed within or otherwise carried by marker material (306).

Cannula (162) may be formed of any suitable metallic or non-metallic material. In some versions, cannula (162) is formed of a thin walled hollow tube formed of a suitable medical grade plastic or polymer. One suitable material is a thermoplastic elastomer, such as Polyether block amide (PEBA), such as is known under the tradename PEBAX. Cannula (162) may be formed of PEBAX and may be substantially transparent to visible light and X-ray.

Side opening (164) may be formed by cutting away a portion of the wall of cannula (162). Side opening (164) communicates with an internal lumen (165) of cannula (162). Side opening (164) may extend axially (in a direction parallel to the axis of lumen (165)) from a proximal opening end (164A) to a distal opening end (164B), as illustrated in FIG. 3.

In the present example, distal tip (172) extends from the distal end of cannula (162) and is rounded as shown in FIG. 3. Referring to FIG. 3, the distal end of cannula (162) is closed by a unitary endpiece (171), with a portion of endpiece (171) extending into internal lumen (165) of cannula (162). Endpiece (171) may be a molded or cast component. Endpiece (171) comprises a tip (172), a ramp (210) having a ramp surface (212), and a marker engaging element (240). Ramp surface (212) aids in directing marker (300) from internal lumen (165) through side opening (164). Marker engaging element (240) helps to retain marker (300) in internal lumen (165) until the user intends to deploy marker (300).

Marker engaging element (240) is disposed within internal lumen (165), and at least a portion of marker engaging element (240) is disposed distally of proximal end (164A) of side opening (164). Marker engaging element (240) extends along a portion of the floor of cannula (162) under opening (164) such that marker engaging element (240) is positioned to reinforce the portion of cannula (162) in which opening (164) is formed. For instance, by positioning marker engaging element (240) underneath opening (164), as shown in FIG. 3, element (240) helps to stiffen cannula (162) in the region where wall of cannula (162) is cut to form opening (164). As shown in FIG. 3, marker engaging element (240) extends from the proximal most portion of ramp surface (212) and does not extend proximally of side opening (164), though in other embodiments, a portion of element (240) may extend proximally of opening (164).

As shown in FIG. 3, marker engaging element (240) is in the form of a step having a generally uniform thickness (T) along element's (240) axial length, except that element (240) has a tapered proximal end (242). Tapered proximal end (242) forms an included angle with the longitudinal axis of lumen (165) (included angle with a horizontal line in FIG. 3) of about 45 degrees, while ramp surface (212) forms an included angle with the longitudinal axis of about 30 degrees. Of course, any number of other suitable angles may be used.

As shown in FIG. 3, an upwardly facing surface (244) (surface facing opening (164)) of marker engaging element (240) extends distally to contact ramp surface (212), so that there is not a space or gap between surface (244) and ramp surface (212). Such an arrangement is advantageous to reduce the possibility that marker (300), upon moving past marker engaging element (240), may become lodged between marker engagement element (240) and ramp (212). In some versions, marker engaging element (240), ramp (210), and/or tip (172) are formed of, or include, a material that is relatively more radiopaque than the wall of cannula (162). For instance, where element (240), ramp (210), and tip (172) are formed as an integral endpiece (171), endpiece (171) may include a radiopaque additive, such as barium sulfate. For instance, endpiece (171) may be a component molded of PEBAX, with about 20 percent by weight barium sulfate added to the molten PEBAX mold composition. The relatively more radiopaque marker engaging element (240), ramp (210), and tip (22) may be useful in distinguishing the position of those components using radiographic imaging. Also, where ramp (210) and/or step of engaging element (240) are positioned in association with opening (164), the addition of a radiopaque material can help identify the position of opening (164), and the position of marker (300) relative to opening (164) before, during, or after deployment of marker (300).

Figure 4:
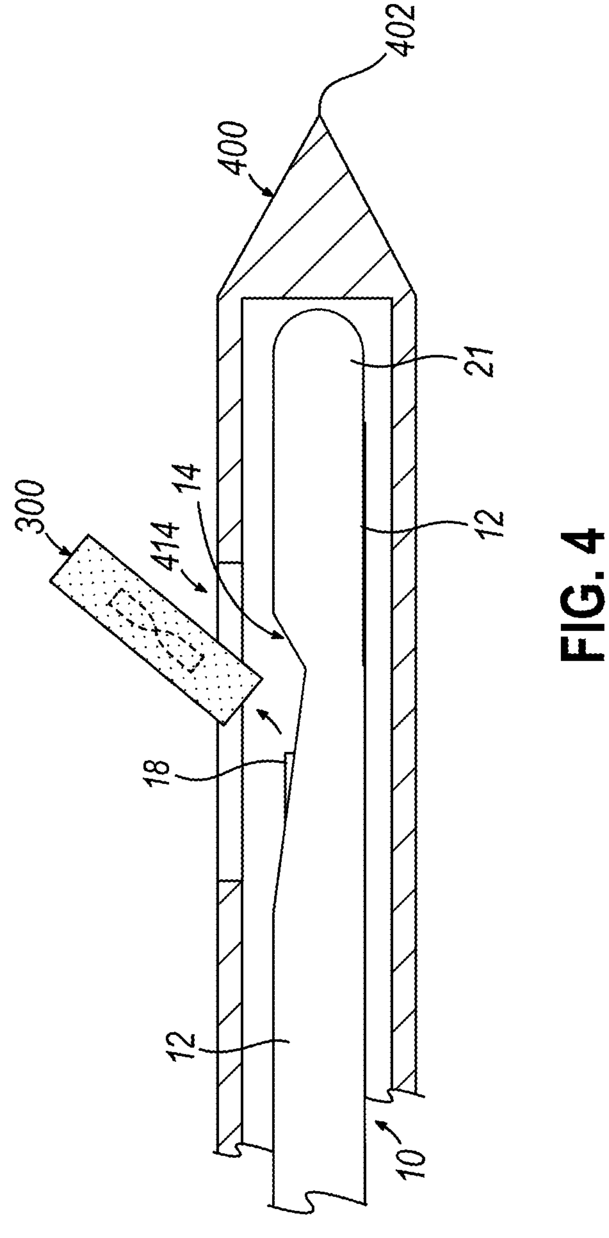
FIG. 4 depicts a cross-sectional view of a marker being deployed from the distal portion of the marker delivery device of FIG. 1 and through a lateral aperture in a biopsy needle to mark a biopsy site.

Referring to FIG. 4, marker delivery device (160) is used to deploy a marker (300) to mark a biopsy location within a patient. In FIG. 4, a cannular biopsy needle (400) is shown having a closed distal end with piercing tip (402) and a lateral tissue receiving aperture (414). Marker delivery device (160) is introduced to a biopsy site through biopsy needle (400), which may be the same needle (400) used to collect a tissue sample from the biopsy site. Biopsy needle (400) may be of the type used with single insertion, multiple sample vacuum assisted biopsy devices. Several such biopsy devices are disclosed in the various patents and patent applications that have been referred to and incorporated by reference herein, though other biopsy devices may be used.

FIG. 4 shows the distal end of marker delivery device (160) disposed within needle (400). Needle (400) may be positioned in tissue, and a biopsy sample may be obtained through lateral aperture (414), thereby providing a biopsy cavity adjacent lateral aperture (414). Then, after the tissue sample has been obtained and transferred proximally through needle (400), and without removing needle (400) from the patient's tissue, marker delivery device (160) is inserted into a proximal opening in needle (400). In FIG. 4, needle (400) and marker delivery device (160) are positioned such that opening (164) of cannula (162) and lateral aperture (414) of needle (400) are substantially aligned axially and circumferentially. Then, with marker delivery device (160) and needle (400) so positioned at the biopsy site, push rod (168) is advanced to deploy marker (300) up ramp surface (212), through opening (164), and then through lateral aperture (414), into the biopsy cavity.

III. EXEMPLARY BIOPSY SITE MARKERS FOR LIMITED MIGRATION

In some examples, it may be desirable to include certain features within a marker similar to marker (100) to reduce the propensity of the marker to migrate when placed within tissue. For instance, some markers may be prone to migration after placement of a biopsy site due to movement of tissue in the intervening time between marker placement and subsequent follow-up procedures. As a result, such markers may introduce challenges with identifying the biopsy site during subsequent follow-up procedures. Accordingly, it may be desirable to incorporate features into a marker similar to marker (100) to maintain the marker in a fixed position within tissue over time. Although several examples are described herein that incorporate the features outlined above, it should be understood that various alternative combinations can be used without departing from the basic principles described herein.

A. Exemplary Marker with Expandable Ends

FIGS. 5 and 6 show an exemplary marker (500) that is generally configured to expand to an irregular shape to thereby anchor marker (500) within tissue. Unless otherwise explicitly noted herein, marker (500) is substantially similar to marker (100) described above. For instance, like with marker (100), marker (500) of the present example includes a marker element (512) and a carrier (520). Marker element (512) of the present example is shown schematically to indicate that a variety of marker elements can be used with marker (500). For instance, in some examples, marker element (512) can be substantially similar to marker element (12) described above. Thus, marker element (512) can be generally configured as non-bioabsorbable and radiopaque and/or echogenic to enhance visualization over time. Similarly, marker element (512) can comprise a variety of materials such as metal, hard plastic, and/or etc.

Marker element (512) can also take on a wide variety of shapes, and/or sizes. For instance, in some examples, marker element (512) can have the shape of marker element (12) shown in FIG. 1 (e.g., a stylized "E" shape). In other examples, marker element (512) can have a helical wire-shape. In yet other examples, marker element (512) can have an irregular shape defining a plurality of reflective surfaces. In still other examples, marker element (512) can be shaped as curved clip. In still other examples, multiple marker elements (512) of varying shapes and/or materials can be used. Of course, still other configurations for marker element (512) may be apparent to those of ordinary skill in the art in view of the teachings herein.

As with carrier (120) described above, carrier (520) of the present example is configured for absorption into a patient after placement of marker (500). However, unlike carrier (120), carrier (520) of the present example includes multiple marker materials (522, 524). Marker materials (522, 524) of the present examples are generally configured to have varying material properties that effect the expansion thereof such that marker (500) can transition from a generally cylindrical shape to a more irregular shape during hydration within tissue. For instance, in the present example an outer marker material (522) is disposed on a distal end and a proximal end of an inner marker material (524). As will be described in greater detail below, outer marker material (522) is generally configured to expand and/or hydrate more quickly relative to inner marker material (524) thereby forming an irregular profile.

Marker materials (522, 524) are generally positioned in an axial layered arrangement. For instance, as shown in FIG. 5, both marker materials (522, 524) form a cylindrical shape when in a dehydrated condition. Thus, marker (500) generally defines an elongate cylindrical configuration. Outer marker material (522) and inner marker material (524) form this configuration by being stacked along the longitudinal axis defined by marker (500). In the present configuration, one section of outer marker material (522) is on each end of inner marker material (524), which is centrally positioned.

It should be understood that marker materials (522, 524) can use a variety of materials having different responses to moisture within tissue. For instance, in the present example outer marker material (522) includes collagen, while inner marker material (524) includes hydrogel. Collagen and hydrogel generally exhibit different physical responses in the presence of moisture. For instance, collagen is generally more prone to rapid absorption of moisture, thereby providing rapid expansion. Meanwhile, hydrogel absorbs moisture at a slower rate, thereby providing slower expansion. For instance, in some examples, collagen can fully expand in approximately 60 seconds, while hydrogel can fully expand in approximately 180 or more minutes depending on the volume of the hydrogel. As will be described in greater detail below, these different properties can be used to influence the shape of marker (500) after marker (500) is placed within tissue. Although certain specific materials are described herein that lead to this effect, it should be understood that various alternative materials or combinations of materials can be used as will be apparent to those of ordinary skill in the art to provide the same effect.

As best seen in FIG. 6, marker element (512) of the present example is generally centered within inner marker material (524). This central configuration can be desirable so that marker element (512) remains centered within a biopsy site as marker materials (522, 524) degrade or absorb into tissue. However, it should be understood that marker element (512) can be placed in various alternative positions either within inner marker material (524) or outer marker material (522). For instance, in some examples, or more marker elements (512) can be placed in a variety of positions either within outer marker material (522), inner marker material (524), or both.

FIG. 7 shows marker (500) in an initially hydrated state after placement within tissue at a biopsy site. In this state, outer marker material (522) absorbs moisture most rapidly and thereby exhibits rapid volumetric expansion. Meanwhile, inner marker material (524) absorbs moisture relatively slowly and thereby exhibits minimal volumetric expansion. In addition, the interfaces between outer marker material (522) and inner marker material (524) can impact the rate of expansion. For instance, in the present example, inner marker material (524) is less prone to rapid expansion and therefore contains at least some of the expansion of outer marker material (522) near the interface.

The expansion properties described above result in a generally irregular shape of marker (500) when in the initially hydrated shape. As a consequence, the difference in size between outer marker material (522) and inner marker material (524) can act as an anchor to hold marker (500) at a given position within tissue. In the present example, an approximate bow tie profile shape is shown as merely an example. Of course, various other alternative profiles can be formed using the present configuration. For instance, in other examples the profile of marker (500) can more closely resemble a dumbbell or various similar shapes. It should be understood that this shape can change throughout the course of hydration of marker (500). For instance, marker (500) can start in the position shown in FIG. 7 after initial hydration. As hydration completes, the profile shape of marker (500) can become less prominent over time as inner marker material (524) hydrates, tissue surrounds marker (500), and/or marker materials (522, 524) begin to absorb/degrade.

B. Exemplary Biopsy Site Marker with Expandable Shell

FIGS. 8 and 9 show an exemplary marker (600) that is generally configured to rapidly expand in volume to thereby anchor marker (600) within tissue. Unless otherwise explicitly noted herein, marker (600) is substantially similar to marker (100) described above. For instance, like with marker (100), marker (600) of the present example includes a marker element (612) and a carrier (620). Marker element (612) of the present example is shown schematically to indicate that a variety of marker element (612) configurations can be used with marker (600). For instance, in some examples, marker element (612) can be substantially similar to marker element (12) described above. Thus, marker element (612) can be generally configured as non-bioabsorbable and radiopaque and/or echogenic to enhance visualization over time. Similarly, marker element (612) can comprise a variety of materials such as metal, hard plastic, and/or etc.

Marker element (612) can also take on a wide variety of shapes, and/or sizes. For instance, in some examples, marker element (612) can have the shape of marker element (12) shown in FIG. 1 (e.g., a stylized "E" shape). In other examples, marker element (612) can have a helical wire-shape. In yet other examples, marker element (612) can have an irregular shape defining a plurality of reflective surfaces. In still other examples, marker element (612) can be shaped as curved clip. In still other examples, multiple marker elements (612) of varying shapes and/or materials can be used. Of course, still other configurations for marker element (612) may be apparent to those of ordinary skill in the art in view of the teachings herein.

As with carrier (120) described above, carrier (620) of the present example is configured for absorption into a patient after placement of marker (600). However, unlike carrier (120), carrier (620) of the present example includes multiple marker materials (622, 624). Marker materials (622, 624) of the present examples are generally configured to have varying material properties that effect the expansion thereof such that marker (600) can rapidly transition from a relatively small or compact volume to a relatively large volume. For instance, in the present example an outer marker material (622) is disposed on an exterior of an inner core of inner marker material (624). As will be described in greater detail below, outer marker material (622) is generally configured to expand and/or hydrate more quickly relative to inner marker material (624) thereby providing a means for rapidly expanding the volume of marker (600).

Marker materials (622, 624) are generally positioned in cored or layered arrangement. For instance, both marker materials (622, 624) form a cylindrical shape when in a dehydrated condition. In this configuration, inner marker material (624) forms an inner cylindrical core that is wrapped by outer marker material (622) also with a cylindrical form. Thus, marker (600) generally defines an elongate cylindrical configuration. In the present configuration, inner marker material (624) is shown as being centrally positioned within outer marker material (622). However, it should be understood that in other examples inner marker material (624) can have a variety of positions within outer marker material (622).

It should be understood that marker materials (622, 624) can use a variety of materials having different responses to moisture within tissue. For instance, in the present example outer marker material (622) includes collagen, while inner marker material (624) includes hydrogel. As described above with respect to marker (500), collagen and hydrogel generally exhibit different physical responses in the presence of moisture. For instance, collagen is generally more prone to rapid absorption of moisture, thereby providing rapid expansion. Meanwhile, hydrogel absorbs moisture at a slower rate, thereby providing slower expansion. As will be described in greater detail below, these different properties can be used to influence the particular way in which marker (600) expands after being placed within tissue. Although certain specific materials are described herein that lead to this effect, it should be understood that various alternative materials or combinations of materials can be used as will be apparent to those of ordinary skill in the art to provide the same effect.

As best seen in FIG. 9, marker element (612) of the present example is generally centered within inner marker material (624). This central configuration can be desirable so that marker element (612) remains centered within a biopsy site as marker materials (622, 624) degrade or absorb into tissue. However, it should be understood that marker element (612) can be placed in various alternative positions either within inner marker material (624) or outer marker material (622). For instance, in some examples, or more marker elements (612) can be placed in a variety of positions either within outer marker material (622) alone, inner marker material (624) alone, or both.

FIG. 10 shows marker (600) in an initially hydrated state after placement within tissue at a biopsy site. In this state, outer marker material (622) absorbs moisture most rapidly and thereby exhibits rapid volumetric expansion. Meanwhile, inner marker material (624) absorbs moisture relatively slowly and thereby exhibits minimal volumetric expansion. These expansion properties, together with the geometry of inner marker material (624) and outer marker material (622), result in marker (600) rapidly expanding in size. In some examples, the volume of marker (600) can expand by approximately 300% or more relative to a compressed or dehydrated state. As a consequence, the rapid volumetric expansion of outer marker material (622) can fill or at least partially fill a biopsy cavity such that outer marker material (622) can act as an anchor to hold marker (600) at a given position within tissue.

In the present example, the approximate profile of marker (600) remains generally cylindrical in shape. Alternatively, the shape of marker (600) after at least some hydration can be characterized as pill-shaped. Of course, various other alternative profiles can be formed using the present configuration. For instance, in other examples the initial geometry of outer marker material (622) can be varied to influence the profile of marker (600) after at least some hydration. In addition, it should be understood that the particular shape and/or size of marker (600) can change throughout the course of hydration. For instance, marker (600) can start in the position shown in FIG. 10 after initial hydration. As hydration completes, marker (600) can exhibit some additional expansion. Subsequently, inner marker material (624) can also expand. In some examples, expansion of inner marker material (624) can lead to enhanced long-term visibility of marker (600) thorough various imaging means such as ultrasound, X-ray, Magnetic Resonance Imaging (MRI), and/or etc. The profile shape and/or size of marker (600) can then become less prominent over time as tissue surrounds marker (600), and/or marker materials (622, 624) begin to absorb/degrade.

C. Exemplary Biopsy Site Marker with Expansion to Dumbbell Shape

Figure 12:
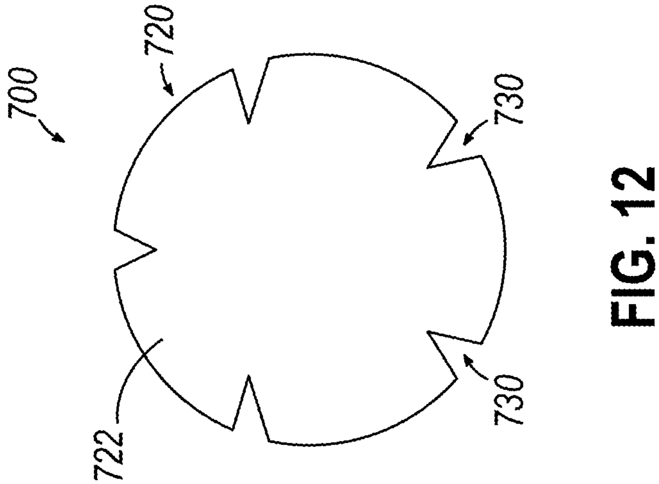
FIG. 12 depicts a front elevational view of the marker of FIG. 11.
Figure 11:
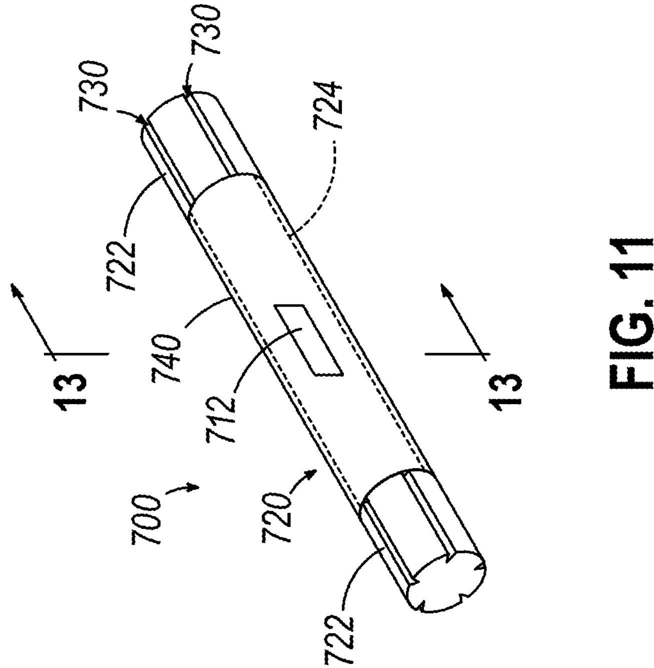
FIG. 11 depicts a perspective view of still another exemplary biopsy site marker.
Figures 13, 14, 15:
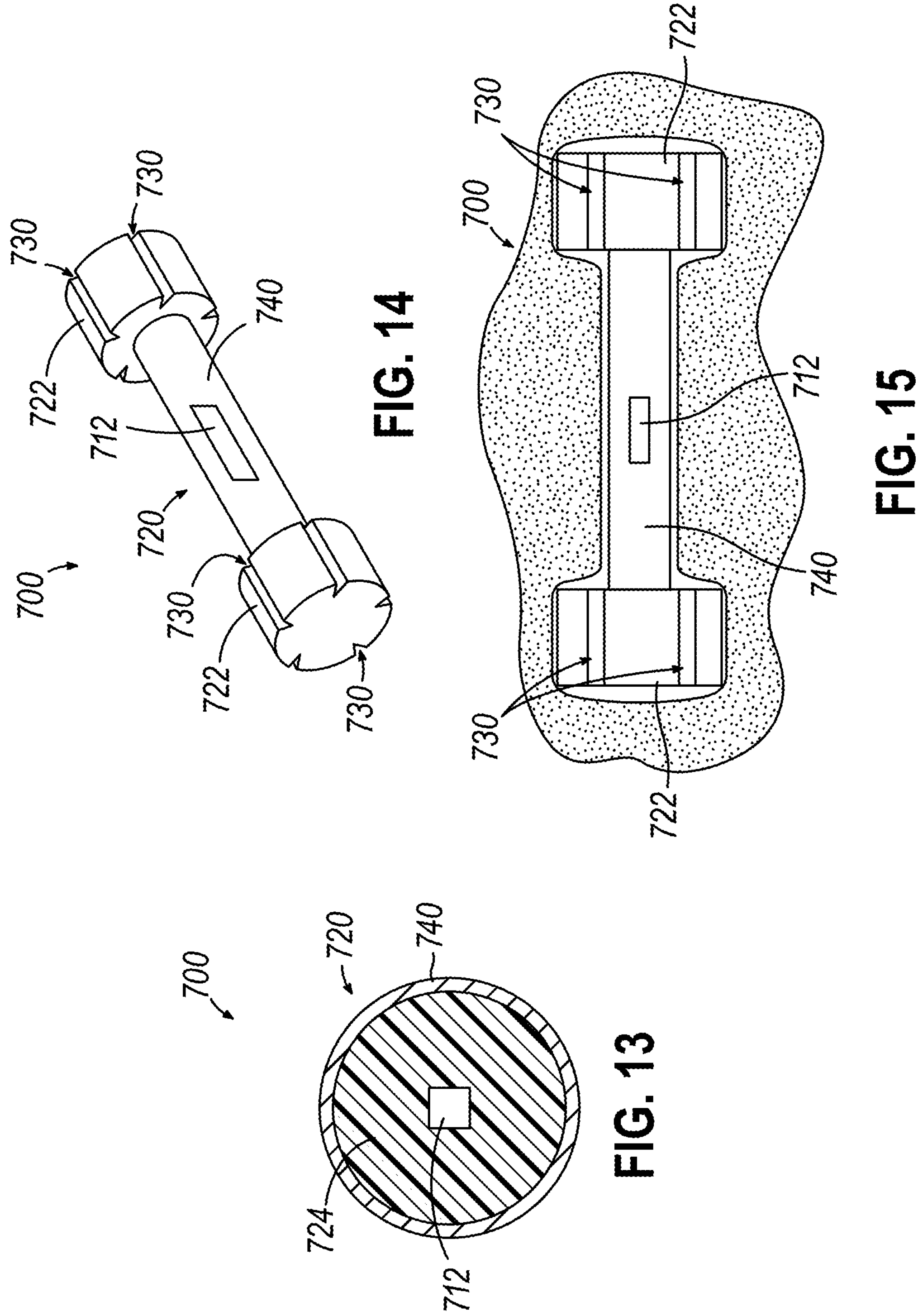
FIG. 13 depicts a cross-sectional view of the marker of FIG. 11, with the cross section taken along line 13-13 of FIG. 11.
FIG. 14 depicts another perspective view of the marker of FIG. 11, with the marker in an initially hydrated state.
FIG. 15 depicts a side elevational view of the marker of FIG. 11 positioned within tissue and in the initially hydrated state.

FIGS. 11 through 13 show an exemplary marker (700) that is generally configured to rapidly expand into a predetermined shape to thereby anchor marker (700) within tissue. Unless otherwise explicitly noted herein, marker (700) is substantially similar to marker (100) described above. For instance, like with marker (100), marker (700) of the present example includes a marker element (712) and a carrier (720). Marker element (712) of the present example is shown schematically to indicate that a variety of marker element (712) configurations can be used with marker (700). For instance, in some examples, marker element (712) can be substantially similar to marker element (12) described above. Thus, marker element (712) can be generally configured as non-bioabsorbable and radiopaque and/or echogenic to enhance visualization over time. Similarly, marker element (712) can comprise a variety of materials such as metal, hard plastic, and/or etc.

Marker element (712) can also take on a wide variety of shapes, and/or sizes. For instance, in some examples, marker element (712) can have the shape of marker element (12) shown in FIG. 1 (e.g., a stylized "E" shape). In other examples, marker element (712) can have a helical wire-shape. In yet other examples, marker element (712) can have an irregular shape defining a plurality of reflective surfaces. In still other examples, marker element (712) can be shaped as curved clip. In still other examples, multiple marker elements (712) of varying shapes and/or materials can be used. Of course, still other configurations for marker element (712) may be apparent to those of ordinary skill in the art in view of the teachings herein.

As with carrier (120) described above, carrier (720) of the present example is configured for absorption into a patient after placement of marker (700). However, unlike carrier (120), carrier (720) of the present example includes multiple marker materials (722, 724). Marker materials (722, 724) of the present examples are generally configured to have varying material properties that effect the expansion thereof such that marker (700) can rapidly transition from an initial shape to a predetermined shape. For instance, in the present example an outer marker material (722) is disposed axially on both a proximal and distal end of inner marker material (724). As will be described in greater detail below, outer marker material (722) is generally configured to expand and/or hydrate more quickly relative to inner marker material (724) thereby providing a means for rapidly expanding the volume of marker (700).

Marker materials (722, 724) are generally positioned in an axial layered arrangement. For instance, as shown in FIG. 11, both marker materials (722, 724) form a cylindrical shape when in a dehydrated condition. Thus, marker (700) generally defines an elongate cylindrical configuration. Outer marker material (722) and inner marker material (724) form this configuration by being stacked along the longitudinal axis defined by marker (700). In the present configuration, one section of outer marker material (722) is on each end of inner marker material (724), which is centrally positioned.

It should be understood that marker materials (722, 724) can use a variety of materials having different responses to moisture within tissue. For instance, in the present example outer marker material (722) includes collagen, while inner marker material (724) includes hydrogel. As described above with respect to marker (500), collagen and hydrogel generally exhibit different physical responses in the presence of moisture. For instance, collagen is generally more prone to rapid absorption of moisture, thereby providing rapid expansion. Meanwhile, hydrogel absorbs moisture at a slower rate, thereby providing slower expansion. As will be described in greater detail below, these different properties can be used to influence the particular way in which marker (700) expands after being placed within tissue. Although certain specific materials are described herein that lead to this effect, it should be understood that various alternative materials or combinations of materials can be used as will be apparent to those of ordinary skill in the art to provide the same effect.

As best seen in FIG. 12, the generally cylindrical shape of outer marker material (722) is interrupted by a plurality of axially extending notches (730). As will be described in greater detail below, notches (730) are generally configured to enhance the grip of tissue with outer marker material (722). Notches (730) of the present example are formed of generally triangular cutouts notched into the outer surface of outer marker material (722). It should be understood that in other examples notches (730) can take on a variety of alternative shapes. For instance, in some examples, notches (730) are rounded, squared, rectangular, and/or etc. In addition, although the present example includes five notches (730) per side, it should be understood that in other examples the particular number of notches (730) can be varied.

As best seen in FIG. 13, marker (700) further includes a restriction cuff (740) that wraps around the exterior of inner marker material (724). Restriction cuff (740) is generally configured to restrict the expansion of inner marker material (724) relative to outer marker material (722). Thus, the shape of marker (700) can also be influenced by mechanical means rather than just variation in material properties between outer marker material (722) and inner marker material (724). Restriction cuff (740) of the present example is formed of a metallic tube or hollow cylinder. However, in other examples various other alternative materials can be used such as polymers and/or plastics.

As will be described in greater detail below, the particular combination of outer marker material (722) being collagen, inner marker material (724) being hydrogel and restriction cuff (740) permits marker (700) to form a dumbbell-shaped profile when at least partially hydrated. Although not shown, it should be understood that the same functional performance can be accomplished using a variety of alternative configurations of outer marker material (722), inner marker material (724), and restriction cuff (740). For instance, in some examples, one end of marker (700) is collagen, while the other end of marker (700) is hydrogel. In other examples, carrier (720) is completely collagen, but restriction cuff (740) is placed at the center with two ends exposed to permit formation of the dumbbell-shaped profile. In yet other examples, carrier (720) is completely hydrogel, but restriction cuff (740) is placed at the center with two ends exposed to permit formation of the dumbbell-shaped profile. In still other examples, carrier (720) is a slurry of collagen and hydrogel combined, but restriction cuff (740) is placed at the center with two ends exposed to permit formation of the dumbbell-shaped profile. Still other configurations will be apparent to those of ordinary skill in the art in view of the teachings herein.

As best seen in FIG. 13, marker element (712) of the present example is generally centered within inner marker material (724). This central configuration can be desirable so that marker element (712) remains centered within a biopsy site as marker materials (722, 724) degrade or absorb into tissue. However, it should be understood that marker element (712) can be placed in various alternative positions either within inner marker material (724) or outer marker material (722). For instance, in some examples, one or more marker elements (712) can be placed in a variety of positions either within outer marker material (722) alone, inner marker material (724) alone, or both.

FIGS. 14 and 15 show marker (700) in an initially hydrated state after placement within tissue at a biopsy site. In this state, outer marker material (722) absorbs moisture most rapidly and thereby exhibits rapid volumetric expansion. Meanwhile, inner marker material (724) absorbs moisture relatively slowly and thereby exhibits minimal volumetric expansion. In addition, restriction cuff (740) further restricts volumetric expansion of inner marker material (724). These expansion properties, together with the geometry of inner marker material (724) and outer marker material (722), result in marker (700) rapidly expanding to form a predetermined shape.

The expansion properties described above result in a generally irregular or dumbbell shape of marker (700) when in the initially hydrated shape. As best seen in FIG. 15, the difference in size between outer marker material (722) and inner marker material (724), as well as the restriction by restriction cuff (740), can act as an anchor to hold marker (700) at a given position within tissue. In the present example, an approximate dumbbell or bow tie profile shape is shown as merely an example. Of course, various other alternative profiles can be formed using the present configuration. It should be understood that this shape can also change throughout the course of hydration of marker (700). For instance, marker (700) can start in the position shown in FIGS. 14 and 15 after initial hydration. As hydration completes, the profile shape of marker (700) can become less prominent over time as inner marker material (724) hydrates, tissue surrounds marker (700), and/or marker materials (722, 724) begin to absorb/degrade.

D. Exemplary Biopsy Site Markers with Combined Carrier

Figures 16, 17, 18:
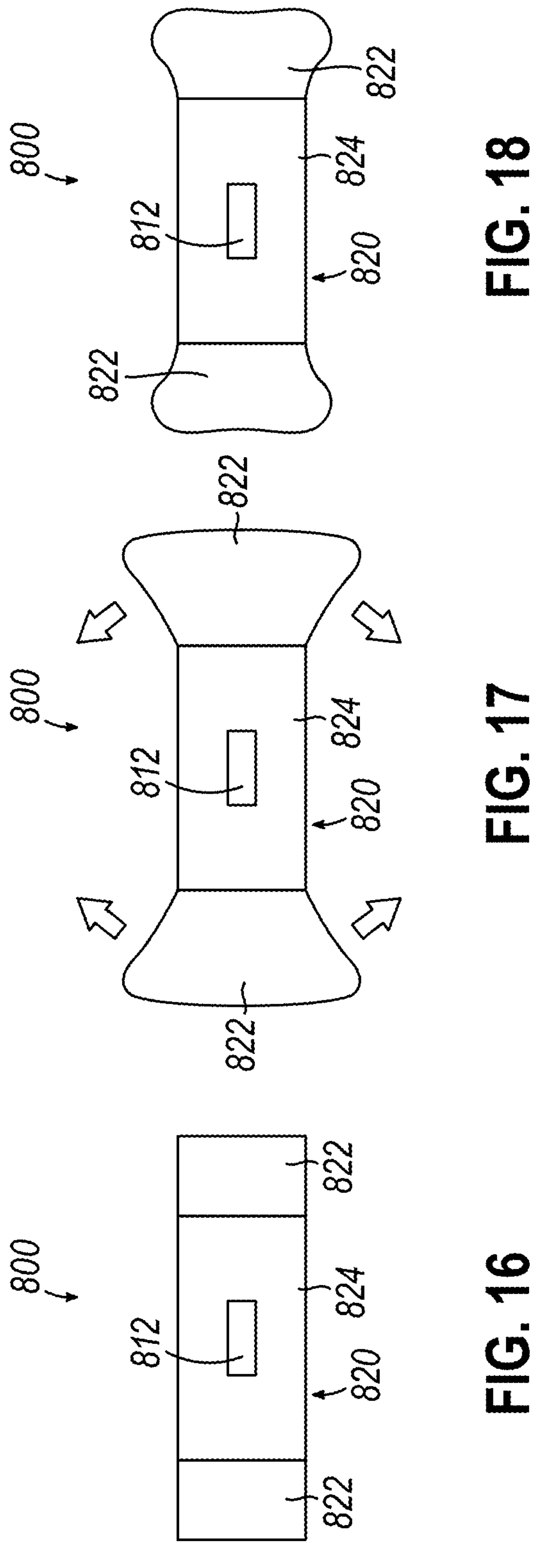
FIG. 16 depicts a side elevational view of still another exemplary biopsy site marker.
FIG. 17 depicts another side elevational view of the marker of FIG. 16, with the marker in an initially hydrated state.
FIG. 18 depicts yet another side elevational view of the marker of FIG. 17, with the marker in a partially absorbed or degraded state.

FIG. 16 shows an exemplary marker (800) that is generally configured to expand to an irregular shape to thereby anchor marker (800) within tissue. Unless otherwise explicitly noted herein, marker (800) is substantially similar to marker (100) described above. For instance, like with marker (100), marker (800) of the present example includes a marker element (812) and a carrier (820). Marker element (812) of the present example is shown schematically to indicate that a variety of marker elements can be used with marker (800). For instance, in some examples, marker element (812) can be substantially similar to marker element (12) described above. Thus, marker element (812) can be generally configured as non-bioabsorbable and radiopaque and/or echogenic to enhance visualization over time. Similarly, marker element (812) can comprise a variety of materials such as metal, hard plastic, and/or etc.

Marker element (812) can also take on a wide variety of shapes, and/or sizes. For instance, in some examples, marker element (812) can have the shape of marker element (12) shown in FIG. 1 (e.g., a stylized “E” shape). In other examples, marker element (812) can have a helical wire-shape. In yet other examples, marker element (812) can have an irregular shape defining a plurality of reflective surfaces. In still other examples, marker element (812) can be shaped as curved clip. In still other examples, multiple marker elements (812) of varying shapes and/or materials can be used. Of course, still other configurations for marker element (812) may be apparent to those of ordinary skill in the art in view of the teachings herein.

As with carrier (120) described above, carrier (820) of the present example is configured for absorption into a patient after placement of marker (800). However, unlike carrier (120), carrier (820) of the present example includes multiple marker materials (822, 824). Marker materials (822, 824) of the present example are generally configured to have varying material properties that effect the expansion thereof such that marker (800) can transition from a generally cylindrical shape to a more irregular shape during hydration within tissue. For instance, in the present example an outer marker material (822) is disposed on a distal end and a proximal end of an inner marker material (824). As will be described in greater detail below, outer marker material (822) is generally configured to expand and/or hydrate more quickly relative to inner marker material (824) thereby forming an irregular profile.

Marker materials (822, 824) are generally positioned in an axial layered arrangement. For instance, both marker materials (822, 824) form a cylindrical shape when in a dehydrated condition. Thus, marker (800) generally defines an elongate cylindrical configuration. Outer marker material (822) and inner marker material (824) form this configuration by being stacked along the longitudinal axis defined by marker (800). In the present configuration, one section of outer marker material (822) is on each end of inner marker material (824), which is centrally positioned.

It should be understood that marker materials (822, 824) can use a variety of materials having different responses to moisture within tissue. For instance, in the present example outer marker material (822) includes collagen, while inner marker material (824) includes hydrogel. Collagen and hydrogel generally exhibit different physical responses in the presence of moisture. For instance, collagen is generally more prone to rapid absorption of moisture, thereby providing rapid expansion. Meanwhile, hydrogel absorbs moisture at a slower rate, thereby providing slower expansion. As will be described in greater detail below, these different properties can be used to influence the shape of marker (800) after marker (800) is placed within tissue. Although certain specific materials are described herein that lead to this effect, it should be understood that various alternative materials or combinations of materials can be used as will be apparent to those of ordinary skill in the art to provide the same effect.

Marker element (812) of the present example is generally centered within inner marker material (824). This central configuration can be desirable so that marker element (812) remains centered within a biopsy site as marker materials (822, 824) degrade or absorb into tissue. However, it should be understood that marker element (812) can be placed in various alternative positions either within inner marker material (824) or outer marker material (822). For instance, in some examples, one or more marker elements (812) can be placed in a variety of positions either within outer marker material (822), inner marker material (824), or both.

FIG. 17 shows marker (800) in an initially hydrated state after placement within tissue at a biopsy site. In this state, outer marker material (822) absorbs moisture most rapidly and thereby exhibits rapid volumetric expansion. Meanwhile, inner marker material (824) absorbs moisture relatively slowly and thereby exhibits minimal volumetric expansion. In addition, the interfaces between outer marker material (822) and inner marker material (824) can impact the rate of expansion. For instance, in the present example, inner marker material (824) is less prone to rapid expansion and therefore contains at least some of the expansion of outer marker material (822) near the interface.

The expansion properties described above result in a generally irregular shape of marker (800) when in the initially hydrated shape. As a consequence, the difference in size between outer marker material (822) and inner marker material (824) can act as an anchor to hold marker (800) at a given position within tissue. In the present example, an approximate bow tie profile shape is shown as merely an example. Of course, various other alternative profiles can be formed using the present configuration. For instance, in other examples the profile of marker (800) can more closely resemble a dumbbell or various similar shapes.

It should be understood that the particular profile shape of marker (800) can change throughout the course of hydration. For instance, marker (800) can start in the position shown in FIG. 17 after initial hydration. As hydration completes, the profile shape of marker (800) can become less prominent over time as inner marker material (824) hydrates, tissue surrounds marker (800), and/or marker materials (822, 824) begin to absorb/degrade.

After hydration of marker (800) is fully complete, some of marker (800) can degrade. For instance, as shown in FIG. 18, outer marker material (822) may begin to degrade first, leaving primarily inner marker material (824) as the predominate structure of carrier (820). Due to the relatively slow moisture absorption rate of inner marker material (824), inner marker material (824) can remain more stable over time. Thus, inner marker material (824) can be used to promote long term visibility of marker (800) under a visualization means such as ultrasound, x-ray, MRI, and/or etc., even when outer marker material (822) has been partially or completely absorbed.

Figure 19:
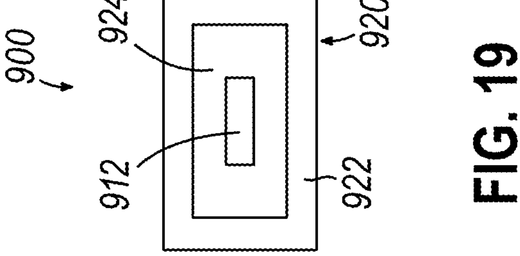
FIG. 19 depicts a side elevational view of still another exemplary biopsy site marker.

FIG. 19 depicts another exemplary marker (900) that is generally configured to rapidly expand in volume to thereby anchor marker (900) within tissue. Unless otherwise explicitly noted herein, marker (900) is substantially similar to marker (800) described above. For instance, like with marker (800), marker (900) of the present example includes a marker element (912) and a carrier (920). Marker element (912) of the present example is substantially similar to marker element (812) described above such that specific details of marker element (912) are not repeated herein.

As with carrier (820) described above, carrier (920) of the present example is configured for absorption into a patient after placement of marker (900) and likewise includes multiple marker materials (922, 924). Like marker materials (822, 824) described above, marker materials (922, 924) have different material properties to influence how marker (900) responds to moisture in the context of hydration. However, unlike marker materials (822, 824) described above, marker materials (922, 924) of the present example are generally configured in a different arrangement. In particular, marker materials (922, 924) are generally positioned in a cored or layered arrangement. In this configuration, an inner marker material (924) forms an inner cylindrical core that is wrapped by an outer marker material (922) also with a cylindrical form. Thus, marker (900) generally defines an elongate cylindrical configuration.

Like with marker materials (822, 824) described above, marker materials (922, 924) can use a variety of materials having different responses to moisture within tissue. For instance, in the present example outer marker material (922) includes collagen, while inner marker material (924) includes hydrogel. As will be described in greater detail below, these different properties can be used to influence the shape of marker (900) after marker (900) is placed within tissue. Although certain specific materials are described herein that lead to this effect, it should be understood that various alternative materials or combinations of materials can be used as will be apparent to those of ordinary skill in the art to provide the same effect.

Figure 20:
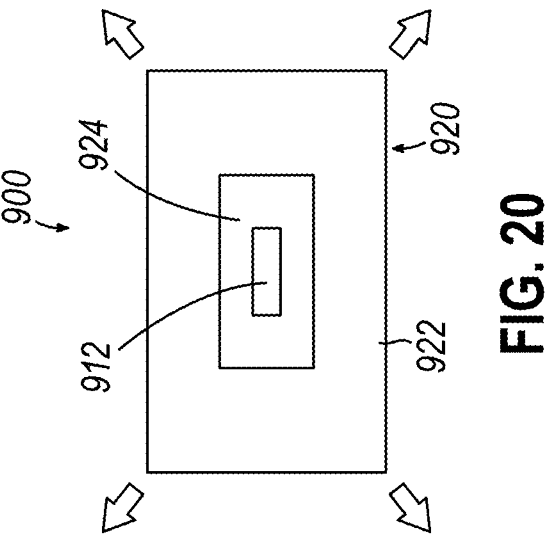
FIG. 20 depicts another side elevational view of the marker of FIG. 19, with the marker in an initially hydrated state.

FIG. 20 shows marker (900) in an initially hydrated state after placement within tissue at a biopsy site. In this state, outer marker material (922) absorbs moisture most rapidly and thereby exhibits rapid volumetric expansion. Meanwhile, inner marker material (924) absorbs moisture relatively slowly and thereby exhibits minimal volumetric expansion. This results in marker (900) rapidly expanding in size while still maintaining a generally cylindrical shape. As a consequence, the increase in size of outer marker material (922) can act as an anchor to hold marker (900) at a given position within tissue.

Figure 21:
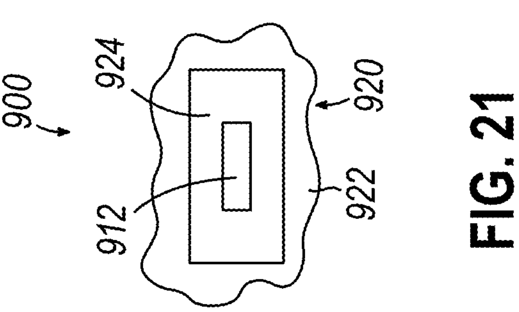
FIG. 21 depicts yet another side elevational view of the marker of FIG. 19, with the marker in a partially absorbed or degraded state.

As shown in FIGS. 20 and 21, the particular profile shape of marker (900) can change throughout the course of hydration. For instance, marker (900) can start in the position shown in FIG. 20 after initial hydration. As hydration completes, the profile shape of marker (900) can become less prominent over time as inner marker material (924) hydrates, tissue surrounds marker (900), and/or marker materials (922, 924) begin to absorb/degrade.

After hydration of marker (900) is fully complete, some of marker (900) material can degrade. For instance, as shown in FIG. 21, outer marker material (922) may begin to degrade first, leaving primarily inner marker material (924) as the predominate structure of carrier (920). Due to the relatively slow moisture absorption rate of inner marker material (924), inner marker material (924) can remain more stable over time. Thus, inner marker material (924) can be used to promote long term visibility of marker (900) under a visualization means such as ultrasound, x-ray, MRI, and/or etc., even when outer marker material (922) has been partially or completely absorbed.

Figure 22:
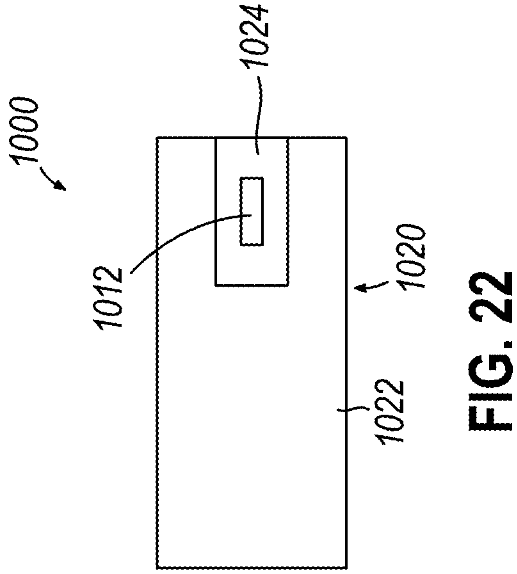
FIG. 22 depicts a side elevational view of still another exemplary biopsy site marker.

FIG. 22 depicts yet another exemplary marker (1000) that is generally configured to rapidly expand in volume to thereby anchor marker (1000) within tissue. Unless otherwise explicitly noted herein, marker (1000) is substantially similar to marker (800) described above. For instance, like with marker (800), marker (1000) of the present example includes a marker element (1012) and a carrier (1020). Marker element (1012) of the present example is substantially similar to marker element (812) described above such that specific details of marker element (1012) are not repeated herein.

As with carrier (820) described above, carrier (1020) of the present example is configured for absorption into a patient after placement of marker (1000) and likewise includes multiple marker materials (1022, 1024). Like marker materials (822, 824) described above, marker materials (1022, 1024) have different material properties to influence how marker (1000) responds to moisture in the context of hydration. However, unlike marker materials (822, 824) described above, marker materials (1022, 1024) of the present example are generally configured in a different arrangement. In particular, marker materials (1022, 1024) are generally positioned in a cored or layered arrangement. In this configuration, an inner marker material (1024) forms an inner cylindrical core that is wrapped by an outer marker material (1022) also with a cylindrical form. Thus, marker (1000) generally defines an elongate cylindrical configuration.

Inner marker material (1024) is axially offset within outer marker material (1022) to one side. In particular, inner marker material (1024) of the present example extends from a distal end of carrier (1020) towards the center of carrier (1020). This configuration may be desirable to control the final placement of marker element (1012) after carrier (1020) has fully absorbed. In addition, or in the alternative, this configuration may be desirable to influence the shape of marker (1000) during hydration, as will be described in greater detail below.

Like with marker materials (822, 824) described above, marker materials (1022, 1024) can use a variety of materials having different responses to moisture within tissue. For instance, in the present example outer marker material (1022) includes collagen, while inner marker material (1024) includes hydrogel. As will be described in greater detail below, these different properties can be used to influence the shape of marker (1000) after marker (1000) is placed within tissue. Although certain specific materials are described herein that lead to this effect, it should be understood that various alternative materials or combinations of materials can be used as will be apparent to those of ordinary skill in the art to provide the same effect.

Figure 23:
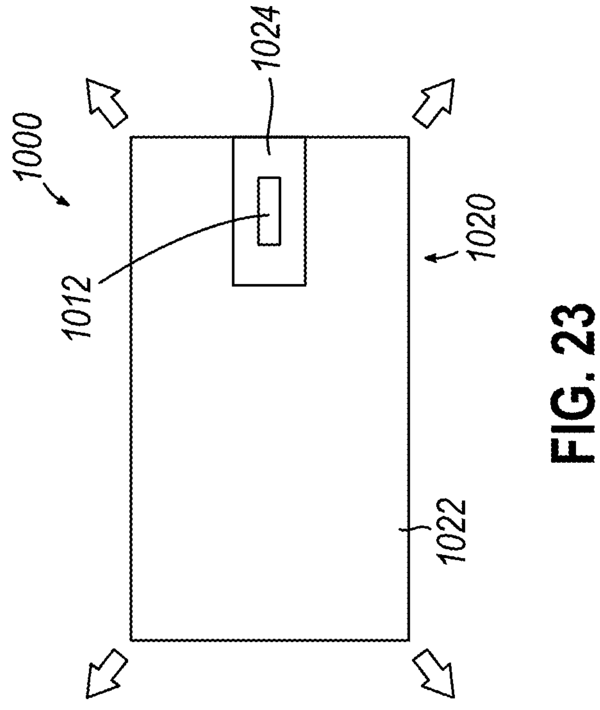
FIG. 23 depicts another side elevational view of the marker of FIG. 22, with the marker in an initially hydrated state.

FIG. 23 shows marker (1000) in an initially hydrated state after placement within tissue at a biopsy site. In this state, outer marker material (1022) absorbs moisture most rapidly and thereby exhibits rapid volumetric expansion. Meanwhile, inner marker material (1024) absorbs moisture relatively slowly and thereby exhibits minimal volumetric expansion. This results in marker (1000) rapidly expanding in size while still maintaining a generally cylindrical shape. As a consequence, the increase in size of outer marker material (1022) can act as an anchor to hold marker (1000) at a given position within tissue.

In some examples, the placement of inner marker material (1024) within outer marker material (1022) can also influence the shape of outer marker material (1022) during expansion. For instance, since inner marker material (1024) is concentrated in one side of carrier (1020), an additional quantity of outer marker material (1022) is included in the opposite side of carrier (1020). Although not shown, it should be understood that, in some examples, this configuration may lead to greater volumetric expansion of carrier (1020) in the side with only outer marker material (1022). Thus, in some examples, marker (1000) can define a more frustoconical shape when initially hydrated rather than a completely cylindrical shape.

As similarly described above, the particular profile shape of marker (1000) can change throughout the course of hydration. For instance, marker (1000) can start in the position shown in FIG. 23 after initial hydration. As hydration completes, the profile shape of marker (1000) can become less prominent over time as inner marker material (1024) hydrates, tissue surrounds marker (1000), and/or marker materials (1022, 1024) begin to absorb/degrade.

After hydration of marker (1000) is fully complete, some of marker (1000) material can degrade. For instance, outer marker material (1022) may begin to degrade first, leaving primarily inner marker material (1024) as the predominate structure of carrier (1020). Due to the relatively slow moisture absorption rate of inner marker material (1024), inner marker material (1024) can remain more stable over time. Thus, inner marker material (1024) can be used to promote long term visibility of marker (1000) under a visualization means such as ultrasound, x-ray, MRI, and/or etc., even when outer marker material (1022) has been partially or completely absorbed.

Figure 24:
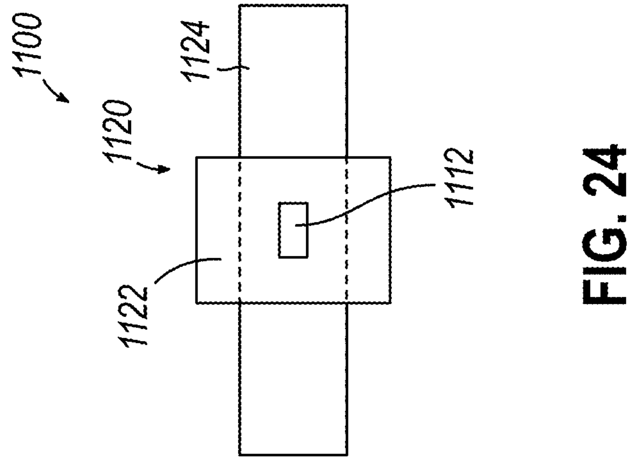
FIG. 24 depicts a side elevational view of still another exemplary biopsy site marker.

FIG. 24 depicts still another exemplary marker (1100) that is generally configured to rapidly expand in volume to thereby anchor marker (1100) within tissue. Unless otherwise explicitly noted herein, marker (1100) is substantially similar to marker (800) described above. For instance, like with marker (800), marker (1100) of the present example includes a marker element (1112) and a carrier (1120). Marker element (1112) of the present example is substantially similar to marker element (812) described above such that specific details of marker element (1112) are not repeated herein.

As with carrier (820) described above, carrier (1120) of the present example is configured for absorption into a patient after placement of marker (1100) and likewise includes multiple marker materials (1122, 1124). Like marker materials (822, 824) described above, marker materials (1122, 1124) have different material properties to influence how marker (1100) responds to moisture in the context of hydration. However, unlike marker materials (822, 824) described above, marker materials (1122, 1124) of the present example are generally configured in a different arrangement. In particular, marker materials (1122, 1124) are generally positioned in a layered arrangement such that a sleeve of outer marker material (1122) surrounds inner marker material (1124). However, it should be understood that marker (1100) still generally defines an elongate cylindrical configuration.

Like with marker materials (822, 824) described above, marker materials (1122, 1124) can use a variety of materials having different responses to moisture within tissue. However, unlike outer marker material (822) and inner marker material (824) described above, outer marker material (1122) and inner marker material (1124) are each respectively different. For instance, in the present example outer marker material (1122) includes hydrogel, while inner marker material (1124) includes collagen. Thus, marker materials (1122, 1124) are reversed relative to marker materials (822, 824) described above. As will be described in greater detail below, the different material properties of hydrogel and collagen can be used to influence the shape of marker (1100) after marker (1100) is placed within tissue. Although certain specific materials are described herein that lead to this effect, it should be understood that various alternative materials or combinations of materials can be used as will be apparent to those of ordinary skill in the art to provide the same effect.

Figure 25:
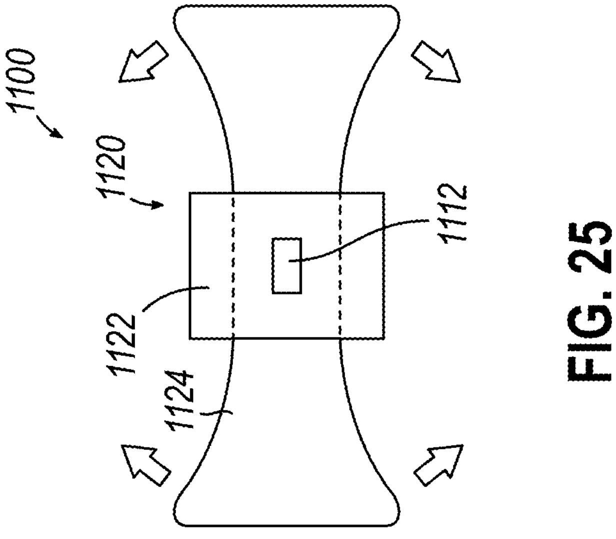
FIG. 25 depicts another side elevational view of the marker of FIG. 24, with the marker in an initially hydrated state.

FIG. 25 shows marker (1100) in an initially hydrated state after placement within tissue at a biopsy site. In this state, inner marker material (1122) (a collagen in the present example) absorbs moisture most rapidly and thereby exhibits its rapid volumetric expansion. Meanwhile, outer marker material (1124) (a hydrogel in the present example) absorbs moisture relatively slowly and thereby exhibits minimal volumetric expansion. This results in marker (1100) rapidly expanding in size. However, unlike marker (800) described above, this rapid expansion is restricted at the center of marker (1100) by outer marker material (1124). This expansion results in marker having a bow tie profile shape, which is shown in FIG. 25. As a consequence, the increase in size of outer marker material (1122), together with the bow tie shape, can act as an anchor to hold marker (1100) at a given position within tissue.

As similarly described above, the particular profile shape of marker (1100) can change throughout the course of hydration. For instance, marker (1100) can start in the position shown in FIG. 25 after initial hydration. As hydration completes, the profile shape of marker (1100) can become less prominent over time as outer marker material (1122) hydrates, tissue surrounds marker (1100), and/or marker materials (1122, 1124) begin to absorb/degrade.

After hydration of marker (1100) is fully complete, some of marker (1100) material can degrade. For instance, inner marker material (1124) may begin to degrade first, leaving primarily outer marker material (1124) as the predominate structure of carrier (1120). Due to the relatively slow moisture absorption rate of outer marker material (1122), outer marker material (1122) can remain more stable over time. Thus, outer marker material (1122) can be used to promote long term visibility of marker (1100) under a visualization means such as ultrasound, x-ray, MRI, and/or etc., even when inner marker material (1124) has been partially or completely absorbed.

E. Exemplary Biopsy Site Marker with Expandable Sides

FIGS. 26 and 27 show an exemplary marker (1200) that is generally configured to expand to an irregular shape to thereby anchor marker (1200) within tissue. Unless otherwise explicitly noted herein, marker (1200) is substantially similar to marker (100) described above. For instance, like with marker (100), marker (1200) of the present example includes a marker element (1212) and a carrier (1220).

Marker element (1212) of the present example is shown schematically to indicate that a variety of marker elements can be used with marker (1200). For instance, in some examples, marker element (1212) can be substantially similar to marker element (12) described above. Thus, marker element (1212) can be generally configured as non-bioabsorbable and radiopaque and/or echogenic to enhance visualization over time. Similarly, marker element (1212) can comprise a variety of materials such as metal, hard plastic, and/or etc.

Marker element (1212) can also take on a wide variety of shapes, and/or sizes. For instance, in some examples, marker element (1212) can have the shape of marker element (12) shown in FIG. 1 (e.g., a stylized "E" shape). In other examples, marker element (1212) can have a helical wire-shape. In yet other examples, marker element (1212) can have an irregular shape defining a plurality of reflective surfaces. In still other examples, marker element (1212) can be shaped as curved clip. In still other examples, multiple marker elements (1212) of varying shapes and/or materials can be used. Of course, still other configurations for marker element (1212) may be apparent to those of ordinary skill in the art in view of the teachings herein.

As with carrier (120) described above, carrier (1220) of the present example is configured for absorption into a patient after placement of marker (1200). However, unlike carrier (120), carrier (1220) of the present example includes multiple marker materials (1222, 1224). Marker materials (1222, 1224) of the present example are generally configured to have varying material properties that effect the expansion thereof such that marker (1200) can transition from a generally cylindrical shape to a more irregular shape during hydration within tissue. For instance, in the present example an outer marker material (1222) is disposed around an inner core of inner marker material (1224). As will be described in greater detail below, outer marker material (1222) is generally configured to expand and/or hydrate more quickly relative to inner marker material (1224) thereby forming an irregular profile.

Marker materials (1222, 1224) are generally positioned in a layered arrangement with outer marker material (1222) as an outer shell and inner marker material (1224) as an inner core. Both marker materials (1222, 1224) form a cylindrical shape when in a dehydrated condition. Thus, marker (1200) generally defines an elongate cylindrical configuration. However, it should be understood that inner marker material (1224) generally has a reduced length relative to outer marker material (1222) such that the distal and proximal ends of carrier (1220) are entirely outer marker material (1222). Thus, in the present configuration, one section of outer marker material (1222) is on each end of inner marker material (1224), which is centrally positioned within outer marker material (1222).

It should be understood that marker materials (1222, 1224) can use a variety of materials having different responses to moisture within tissue. For instance, in the present example outer marker material (1222) includes collagen, while inner marker material (1224) includes hydrogel. Collagen and hydrogel generally exhibit different physical responses in the presence of moisture. For instance, collagen is generally more prone to rapid absorption of moisture, thereby providing rapid volumetric expansion. Meanwhile, hydrogel absorbs moisture at a slower rate, thereby providing slower expansion. As will be described in greater detail below, these different properties can be used to influence the shape of marker (1200) after marker (1200) is placed within tissue. Although certain specific materials are described herein that lead to this effect, it should be understood that various alternative materials or combinations of materials can be used as will be apparent to those of ordinary skill in the art to provide the same effect.

Marker element (1212) of the present example is generally centered within inner marker material (1224). This central configuration can be desirable so that marker element (1212) remains centered within a biopsy site as marker materials (1222, 1224) degrade or absorb into tissue. However, it should be understood that marker element (1212) can be placed in various alternative positions either within inner marker material (1224) or outer marker material (1222). For instance, in some examples, one or more marker elements (1212) can be placed in a variety of positions either within outer marker material (1222), inner marker material (1224), or both.

FIG. 28 shows marker (1200) in an initially hydrated state after placement within tissue at a biopsy site. In this state, outer marker material (1222) absorbs moisture most rapidly and thereby exhibits rapid volumetric expansion. Meanwhile, inner marker material (1224) absorbs moisture relatively slowly and thereby exhibits minimal volumetric expansion. These differing expansion properties between marker materials (1222, 1224) can influence the shape of marker (1200) as marker (1200) absorbs moisture. For instance, in the present example, inner marker material (1224) occupies a substantial portion of the central volume of carrier (1220). As a result, the central portion of carrier (1220) may expand less relative to the distal and proximal ends of carrier (1220).

The expansion properties described above result in a generally irregular shape of marker (1200) when in the initially hydrated shape. This shape generally corresponds to that of a bow tie or dumbbell. As a consequence, the difference in size or diameter between the ends of carrier (1220) and the central portion of carrier (1220) can act as an anchor to hold marker (1200) at a given position within tissue. In the present example, the approximate bow tie profile shape is shown as merely an example. Of course, various other alternative profiles can be formed using the present configuration. For instance, in other examples the profile of marker (1200) can more closely resemble a dumbbell or various similar shapes.

It should be understood that the particular profile shape of marker (1200) can change throughout the course of hydration. For instance, marker (1200) can start in the position shown in FIG. 28 after initial hydration. As hydration completes, the profile shape of marker (1200) can become less prominent over time as inner marker material (1224) hydrates, tissue surrounds marker (1200), and/or marker materials (1222, 1224) begin to absorb/degrade.

After hydration of marker (1200) is fully complete, some of marker (1200) can degrade. For instance, outer marker material (1222) may begin to degrade first, leaving primarily inner marker material (1224) as the predominate structure of carrier (1220). Due to the relatively slow moisture absorption rate of inner marker material (1224), inner marker material (1224) can remain more stable over time. Thus, inner marker material (1224) can be used to promote long term visibility of marker (1200) under a visualization means such as ultrasound, x-ray, MRI, and/or etc., even when outer marker material (1222) has been partially or completely absorbed.

F. Exemplary Biopsy Site Marker with Expandable Plug

Figure 29:
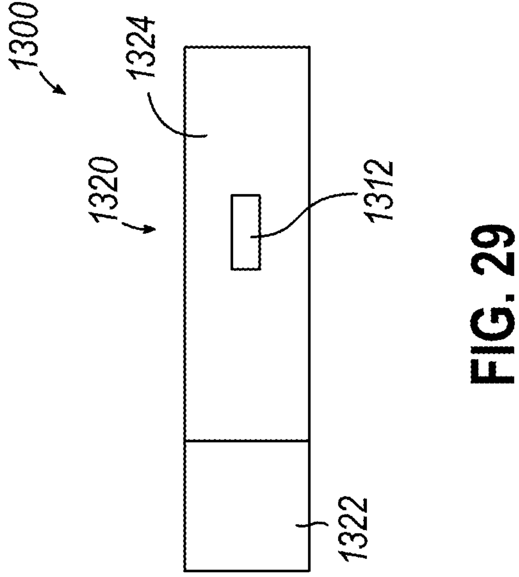
FIG. 29 depicts a top plan view of still another exemplary biopsy site marker.

FIG. 29 shows an exemplary marker (1300) that is generally configured to rapidly expand into a predetermined shape to thereby anchor marker (1300) within tissue. Unless otherwise explicitly noted herein, marker (1300) is substantially similar to marker (100) described above. For instance, like with marker (100), marker (1300) of the present example includes a marker element (1312) and a carrier (1320). Marker element (1312) of the present example is shown schematically to indicate that a variety of marker element (1312) configurations can be used with marker (1300). For instance, in some examples, marker element (1312) can be substantially similar to marker element (12) described above. Thus, marker element (1312) can be generally configured as non-bioabsorbable and radiopaque and/or echogenic to enhance visualization over time. Similarly, marker element (1312) can comprise a variety of materials such as metal, hard plastic, and/or etc.

Marker element (1312) can also take on a wide variety of shapes, and/or sizes. For instance, in some examples, marker element (1312) can have the shape of marker element (12) shown in FIG. 1 (e.g., a stylized "E" shape). In other examples, marker element (1312) can have a helical wire-shape. In yet other examples, marker element (1312) can have an irregular shape defining a plurality of reflective surfaces. In still other examples, marker element (1312) can be shaped as curved clip. In still other examples, multiple marker elements (1312) of varying shapes and/or materials can be used. Of course, still other configurations for marker element (1312) may be apparent to those of ordinary skill in the art in view of the teachings herein.

As with carrier (120) described above, carrier (1320) of the present example is configured for absorption into a patient after placement of marker (1300). However, unlike carrier (120), carrier (1320) of the present example includes multiple marker materials (1322, 1324). Marker materials (1322, 1324) of the present examples are generally configured to have varying material properties that effect the expansion thereof such that marker (1300) can rapidly transition from an initial shape to a predetermined shape.

Marker materials (1322, 1324) are generally positioned in an axially layered arrangement. For instance, both marker materials (1322, 1324) form a cylindrical shape when in a dehydrated condition. Thus, marker (1300) generally defines an elongate cylindrical configuration. Marker materials (1322, 1324) include a plug marker material (1322) and a core marker material (1324). Plug marker material (1322) and core marker material (1324) together define the shape of carrier (1320) by being stacked in an end-to-end configuration along the longitudinal axis defined by marker (1300). In the present configuration, plug marker material (1322) is isolated to a single end of core marker material (1324). However, it should be understood that in other examples, plug marker material (1322) can be on both ends of core marker material (1324).

It should be understood that marker materials (1322, 1324) can use a variety of materials having different responses to moisture within tissue. For instance, in the present example plug marker material (1322) includes collagen, while core marker material (1324) includes hydrogel. As described above with respect to marker (500), collagen and hydrogel generally exhibit different physical responses in the presence of moisture. For instance, collagen is generally more prone to rapid absorption of moisture, thereby providing rapid expansion. Meanwhile, hydrogel absorbs moisture at a slower rate, thereby providing slower expansion. As will be described in greater detail below, these different properties can be used to influence the particular way in which marker (1300) expands after being placed within tissue. Although certain specific materials are described herein that lead to this effect, it should be understood that various alternative materials or combinations of materials can be used as will be apparent to those of ordinary skill in the art to provide the same effect.

Marker element (1312) of the present example is generally centered within core marker material (1324). This central configuration can be desirable so that marker element (1312) remains centered or otherwise in position within a biopsy site as marker materials (1322, 1324) degrade or absorb into tissue. However, it should be understood that marker element (1312) can be placed in various alternative positions either within core marker material (1324) or plug marker material (1322). For instance, in some examples, one or more marker elements (1312) can be placed in a variety of positions either within plug marker material (1322) alone, core marker material (1324) alone, or both.

Figure 30:
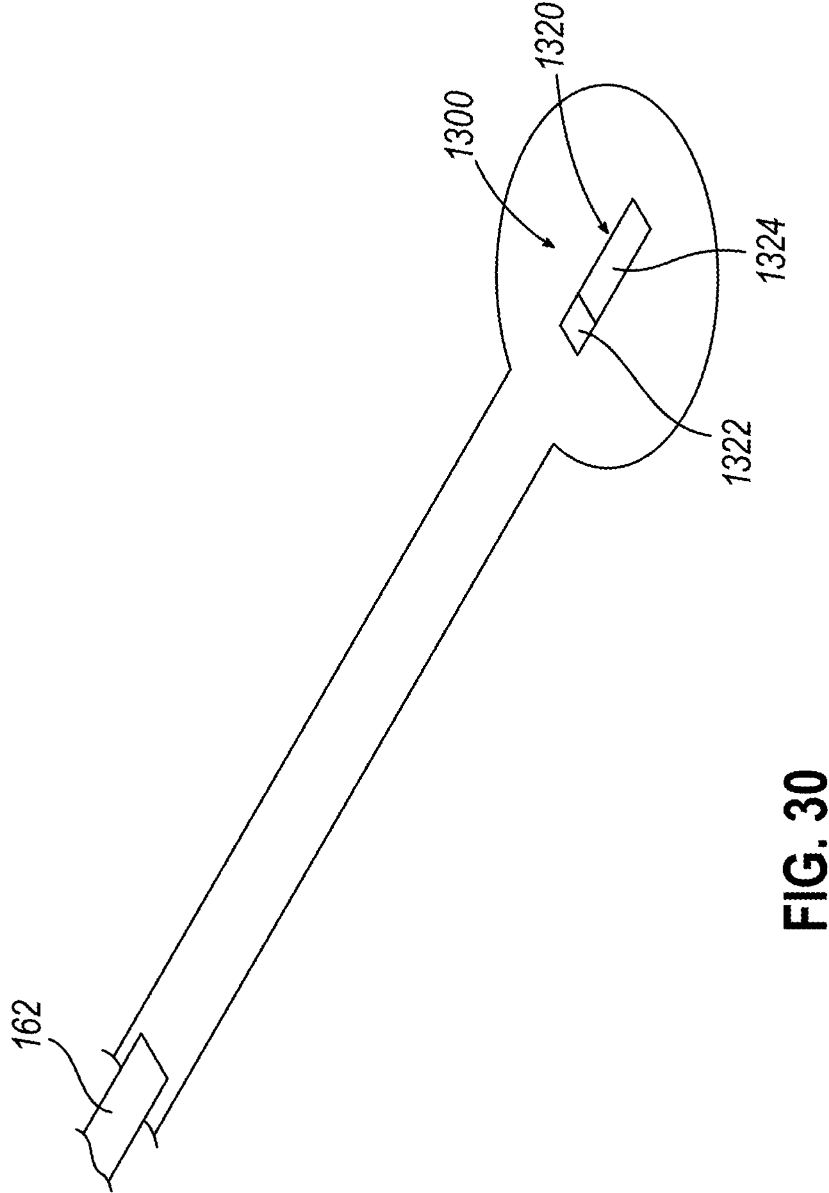
FIG. 30 depicts another top plan view of the marker of FIG. 29, with the marker deployed at a biopsy site.
Figure 31:
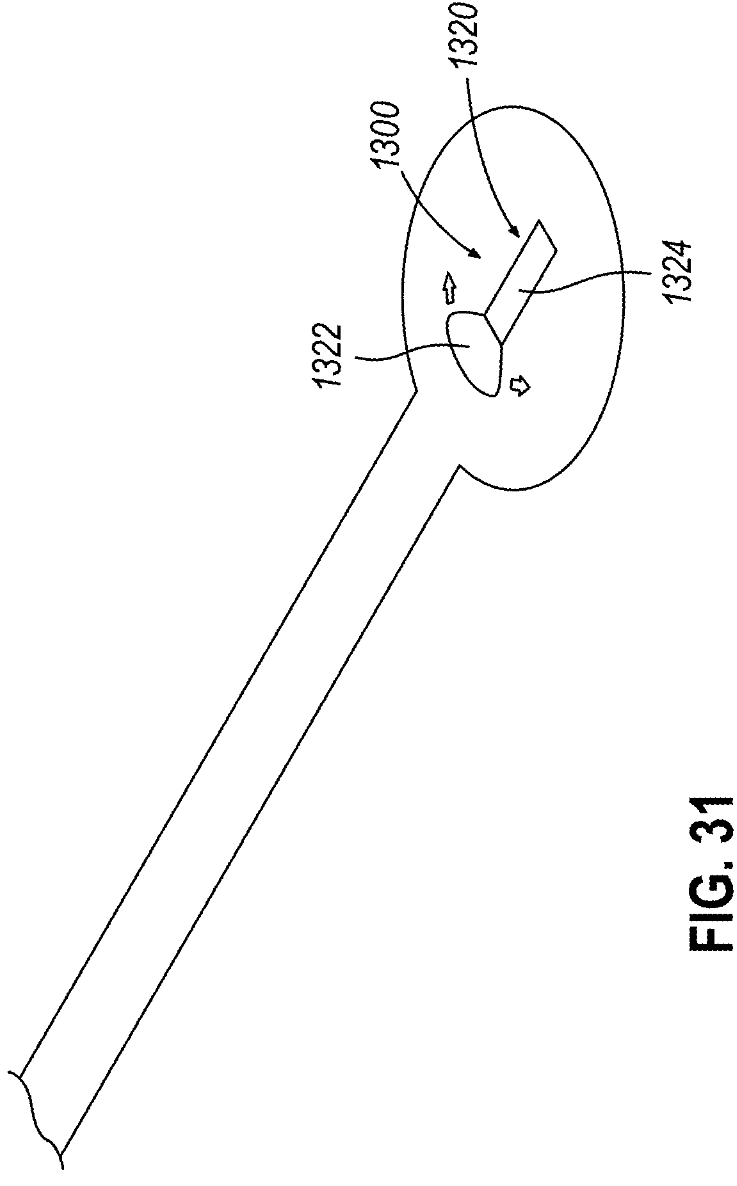
FIG. 31 depicts yet another top plan view of the marker of FIG. 29, with the marker in an initially hydrated state at the biopsy site.

FIGS. 30 and 31 show an exemplary use of marker (1300). As best seen in FIG. 30, marker (1300) can be initially deployed at a biopsy site using cannula (162) of marker delivery device (150) or any other suitable marker delivery device. Deployment can occur through a lumen or other passage formed in tissue by a biopsy needle or other instrument.

Once marker (1300) is deployed, marker (1300) begins to absorb moisture in marker materials (1322, 1324). FIG. 31 shows marker (1300) in an initially hydrated state after placement within tissue at a biopsy site. In this state, plug marker material (1322) absorbs moisture rapidly and thereby exhibits rapid volumetric expansion. Meanwhile, core marker material (1324) absorbs moisture relatively slowly and thereby exhibits minimal volumetric expansion. These expansion properties, together with the relative positioning of plug marker material (1324) and core marker material (1322), result in marker (1300) rapidly expanding to form a predetermined shape.

The expansion properties described above result in a generally pie or mushroom-shaped profile of marker (1300) when in the initially hydrated shape. As best seen in FIG. 31, plug marker material (1322) has rapidly expanded in shape to a relatively large diameter to thereby occupy a relatively large volume. Meanwhile, core marker material (1324) has undergone a relatively minimal expansion to maintain a relatively small diameter. In this configuration, plug marker material (1322) can act as a plug to prevent marker (1300) from following the passage created by the biopsy needle. Thus, the rapid expansion of plug marker material (1322) can act to hold marker (1300) within the biopsy cavity and at the biopsy site.

It should be understood that the particular shape of marker (1300) can also change throughout the course of hydration. For instance, marker (1300) can start in the position shown in FIG. 31 after initial hydration. As hydration completes, the profile shape of marker (1300) can become less prominent over time as core marker material (1324) hydrates, tissue surrounds marker (1300), and/or marker materials (1322, 1324) begin to absorb/degrade.

G. Exemplary Biopsy Site Marker with Asymmetric Expansion

Figures 32, 33, 34:
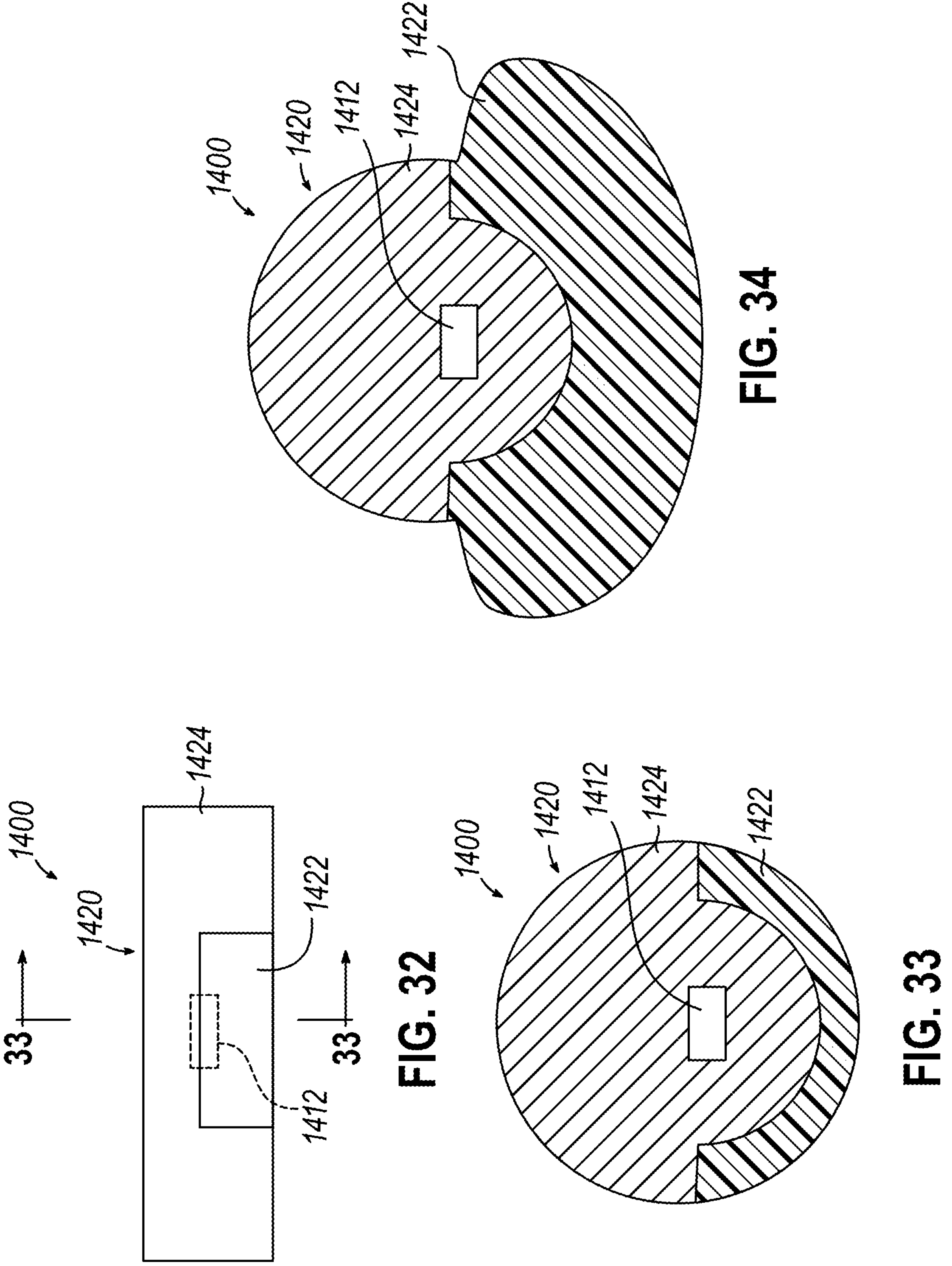
FIG. 32 depicts a side elevational view of still another exemplary biopsy site marker.
FIG. 33 depicts a cross-sectional view of the marker of FIG. 32, with the cross-section taken along line 33-33 of FIG. 32.
FIG. 34 depicts another cross-sectional view of the marker of FIG. 32, with the marker in an initially hydrated state.

FIGS. 32 and 33 show an exemplary marker (1400) that is generally configured to rapidly expand in volume to a predetermined asymmetric configuration and thereby anchor marker (1400) within tissue. Unless otherwise explicitly noted herein, marker (1400) is substantially similar to marker (100) described above. For instance, like with marker (100), marker (1400) of the present example includes a marker element (1412) and a carrier (1420). Marker element (1412) of the present example is shown schematically to indicate that a variety of marker element (1412) configurations can be used with marker (1400). For instance, in some examples, marker element (1412) can be substantially similar to marker element (12) described above. Thus, marker element (1412) can be generally configured as non-bioabsorbable and radiopaque and/or echogenic to enhance visualization over time. Similarly, marker element (1412) can comprise a variety of materials such as metal, hard plastic, and/or etc.

Marker element (1412) can also take on a wide variety of shapes, and/or sizes. For instance, in some examples, marker element (1412) can have the shape of marker element (12) shown in FIG. 1 (e.g., a stylized "E" shape). In other examples, marker element (1412) can have a helical wire-shape. In yet other examples, marker element (1412) can have an irregular shape defining a plurality of reflective surfaces. In still other examples, marker element (1412) can be shaped as curved clip. In still other examples, multiple marker elements (1412) of varying shapes and/or materials can be used. Of course, still other configurations for marker element (1412) may be apparent to those of ordinary skill in the art in view of the teachings herein.

As with carrier (120) described above, carrier (1420) of the present example is configured for absorption into a patient after placement of marker (1400). However, unlike carrier (120), carrier (1420) of the present example includes multiple marker materials (1422, 1424). Marker materials (1422, 1424) of the present example are generally configured to have varying material properties that effect the expansion thereof such that marker (1400) can rapidly transition from a relatively small or compact volume to a relatively large volume with an asymmetric shape. For instance, in the present example, an outer marker material (1422) is disposed on a single side of an inner core of inner marker material (1424). As will be described in greater detail below, outer marker material (1422) is generally configured to expand and/or hydrate more quickly relative to inner marker material (1424) thereby providing a means for rapidly expanding the volume of a portion of marker (1400).

Marker materials (1422, 1424) are generally positioned in cored or layered arrangement. In particular, inner marker material (1424) generally defines a cylindrical configuration with an indentation near the center of carrier (1420). Outer marker material (1422) is positioned within the indentation near the center of carrier (1420). Outer marker material (1422) is also flush with the outer surface of inner marker material (1424) such that inner marker material (1424) and outer marker material (1422) together define a cylindrical shape when marker (1400) is in a dehydrated configuration. Thus, marker (1400) generally defines an elongate cylindrical configuration when in the dehydrated configuration. Although outer marker material (1422) is shown as being generally centrally positioned relative to inner marker material (1424), it should be understood that in other examples outer marker material (1422) can have a variety of positions relative to inner marker material (1424).

Marker materials (1422, 1424) can use a variety of materials having different responses to moisture within tissue. For instance, in the present example outer marker material (1422) includes collagen, while inner marker material (1424) includes hydrogel. As described above with respect to marker (500), collagen and hydrogel generally exhibit different physical responses in the presence of moisture. For instance, collagen is generally more prone to rapid absorption of moisture, thereby providing rapid expansion. Meanwhile, hydrogel absorbs moisture at a slower rate, thereby providing slower expansion. As will be described in greater detail below, these different properties can be used to influence the particular way in which marker (1400) expands after being placed within tissue. Although certain specific materials are described herein that lead to this effect, it should be understood that various alternative materials or combinations of materials can be used as will be apparent to those of ordinary skill in the art to provide the same effect.

As best seen in FIG. 33, marker element (1412) of the present example is generally centered within carrier (1420) and is disposed within inner marker material (1424). This central configuration can be desirable so that marker element (1412) remains centered within a biopsy site as marker materials (1422, 1424) degrade or absorb into tissue. However, it should be understood that marker element (1412) can be placed in various alternative positions either within inner marker material (1424) or outer marker material (1422). For instance, in some examples or more marker elements (1412) can be placed in a variety of positions either within outer marker material (1422) alone, inner marker material (1424) alone, or both.

FIG. 34 shows marker (1400) in an initially hydrated state after placement within tissue at a biopsy site. In this state, outer marker material (1422) absorbs moisture most rapidly and thereby exhibits rapid volumetric expansion. Meanwhile, inner marker material (1424) absorbs moisture relatively slowly and thereby exhibits minimal volumetric expansion. These expansion properties, together with the geometry and relative positioning of inner marker material (1424) and outer marker material (1422), result in marker (1400) rapidly expanding in size to a predetermined asymmetric shape. As a consequence, the rapid volumetric expansion of outer marker material (1422) can fill or at least partially fill a biopsy cavity such that outer marker material (1422) can act as an anchor to hold marker (1400) at a given position within tissue.

In the present example, the approximate profile of marker (1400) remains partially cylindrical in shape, but outer marker material (1422) bulges out from inner marker material (1424) to form a generally asymmetrical profile. As a result, the bulge of outer marker material (1422) can act to anchor marker (1400) within tissue. Of course, various other alternative profiles can be formed using the present configuration. For instance, in other examples the relative positioning of outer marker material (1422) and inner marker material (1424) can be varied to influence the profile of marker (1400) after at least some hydration. By way of example only, in such examples, outer marker material (1422) can be offset to one side of inner marker material (1424) or another to cause one side of marker (1400) to expand relative to another. In addition, or in the alternative, the particular size of outer marker material (1422) relative to inner marker material (1424) can be varied to increase or decrease the size of the bulge formed by outer marker material (1422). Of course, various alternative configurations of outer marker material (1422) and inner marker material (1424) will be apparent to those of ordinary skill in the art in view of the teachings herein.

It should be understood that the particular shape and/or size of marker (1400) can change throughout the course of hydration. For instance, marker (1400) can start in the position shown in FIG. 34 after initial hydration. As hydration completes, marker (1400) can exhibit some additional expansion. Subsequently, inner marker material (1424) can also expand. In some examples, expansion of inner marker material (1424) can lead to enhanced long-term visibility of marker (1400) thorough various imaging means such as ultrasound, X-ray, Magnetic Resonance Imaging (MRI), and/or etc. The profile shape and/or size of marker (1400) can then become less prominent over time as tissue surrounds marker (1400), and/or marker materials (1422, 1424) begin to absorb/degrade.

H. Exemplary Biopsy Site Marker with Insertable Pellet

Figure 35:
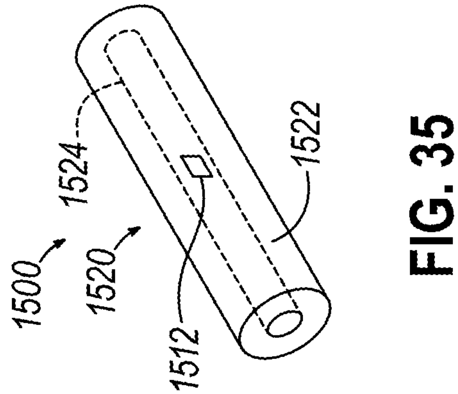
FIG. 35 depicts a perspective view of still another exemplary biopsy site marker.

FIG. 35 shows an exemplary marker (1500) that is generally configured to rapidly expand in volume to thereby anchor marker (1500) within tissue. Unless otherwise explicitly noted herein, marker (1500) is substantially similar to marker (600) described above. For instance, like with marker (600), marker (1500) of the present example includes a marker element (1512) and a carrier (1520). Marker element (1512) of the present example is substantially similar to marker element (612) described above such that specific details of marker element (1512) are not repeated herein.

As with carrier (620) described above, carrier (1520) of the present example is configured for absorption into a patient after placement of marker (1500). Also like carrier (620), carrier (1520) of the present example includes multiple marker materials (1522, 1524). Like with marker materials (622, 624), marker materials (1522, 1524) of the present example are generally configured to have varying material properties that effect the expansion thereof such that marker (1500) can rapidly transition from a relatively small or compact volume to a relatively large volume. However, unlike marker materials (622, 624), marker materials (1522, 1524) are generally configured to be separable from each other. As will be described in greater detail below, this configuration can be desirable for assembly purposes. Although, marker materials (1522, 1524) are separable from each other, they nonetheless have a similar dehydrated configuration and material properties relative to marker materials (622, 624) described above. For instance, in the present example an outer marker material (1522) is disposed on an exterior of an inner core of inner marker material (1524). As will be described in greater detail below, outer marker material (1522) is generally configured to expand and/or hydrate more quickly relative to inner marker material (1524) thereby providing a means for rapidly expanding the volume of marker (1500).

Marker materials (1522, 1524) are generally positioned in cored or layered arrangement. For instance, both marker materials (1522, 1524) form a cylindrical shape when in a dehydrated condition. In this configuration, inner marker material (1524) forms an inner cylindrical core that is wrapped by outer marker material (1522) also with a cylindrical form. Thus, marker (1500) generally defines an elongate cylindrical configuration. In the present configuration, inner marker material (1524) is shown as being centrally positioned within outer marker material (1522). However, it should be understood that in other examples inner marker material (1524) can have a variety of positions within outer marker material (1522).

It should be understood that marker materials (1522, 1524) can use a variety of materials having different responses to moisture within tissue. For instance, in the present example outer marker material (1522) includes collagen, while inner marker material (1524) includes hydrogel. As described above with respect to marker (600), collagen and hydrogel generally exhibit different physical responses in the presence of moisture. For instance, collagen is generally more prone to rapid absorption of moisture, thereby providing rapid expansion. Meanwhile, hydrogel absorbs moisture at a slower rate, thereby providing slower expansion. As will be described in greater detail below, these different properties can be used to influence the particular way in which marker (1500) expands after being placed within tissue. Although certain specific materials are described herein that lead to this effect, it should be understood that various alternative materials or combinations of materials can be used as will be apparent to those of ordinary skill in the art to provide the same effect.

Like with marker (600) described above, marker (1500) of the present example can transition from the dehydrated configuration shown in FIG. 35 to an expanded initially hydrated state of configuration after placement within tissue at a biopsy site. As similarly described above, outer marker material (1522) absorbs moisture most rapidly during the transition from the dehydrated state to the initially hydrated state to thereby exhibit rapid volumetric expansion. Meanwhile, inner marker material (1524) absorbs moisture relatively slowly and thereby exhibits minimal volumetric expansion. These expansion properties, together with the geometry of inner marker material (1524) and outer marker material (1522), result in marker (1500) rapidly expanding in size. As a consequence, the rapid volumetric expansion of outer marker material (1522) can fill or at least partially fill a biopsy cavity such that outer marker material (1522) can act as an anchor to hold marker (1500) at a given position within tissue.

Figure 36:
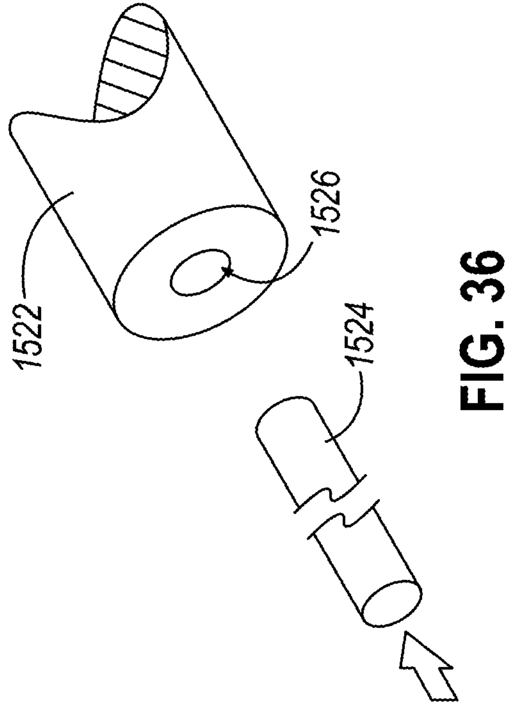
FIG. 36 depicts a partial perspective exploded view of the marker of FIG. 35.

FIG. 36 shows marker (1500) in an assembly state. As can be seen, inner marker material (1524) is initially configured as a cylindrical pellet separate from outer marker material (1522). Outer marker material (1524) is also cylindrical in shape with a central void (1526) configured for receiving inner marker material (1524). In an exemplary manufacturing operation, outer marker material (1522) can be first manufactured with collagen using a mandrel or other structure to form void (1526). Inner marker material (1524) can be pre-manufactured as a hydrogel pellet or insert. Inner marker material (1524) can then be inserted into void (1526) of outer marker material (1522). After inner marker material (1524) is inserted into outer marker material (1522), the combination of inner marker material (1524) and outer marker material (1522) can be compressed.

In an alternative manufacturing operation, outer marker material (1522) can be initially manufactured using collagen with a plurality of fibrous areas or voids. Inner marker material (1524) can be in the form of a liquid hydrogel for injection into the fibrous areas or voids. The combination of inner marker material (1524) and outer marker material (1522) can then be compressed.

In another alternative manufacturing operation, outer marker material (1522) can include void (1526) as shown above, or a plurality of voids (1526). Inner marker material (1524) can be pre-manufactured as a plurality of hydrogel pellets. Each pellet of inner marker material (1524) can then be inserted into outer marker material (1522) to fill void (1526) or the plurality of voids (1526). The combination of inner marker material (1524) and outer marker material (1522) can then be compressed.

I. Exemplary Two-Part Biopsy Site Marker

Figure 37:
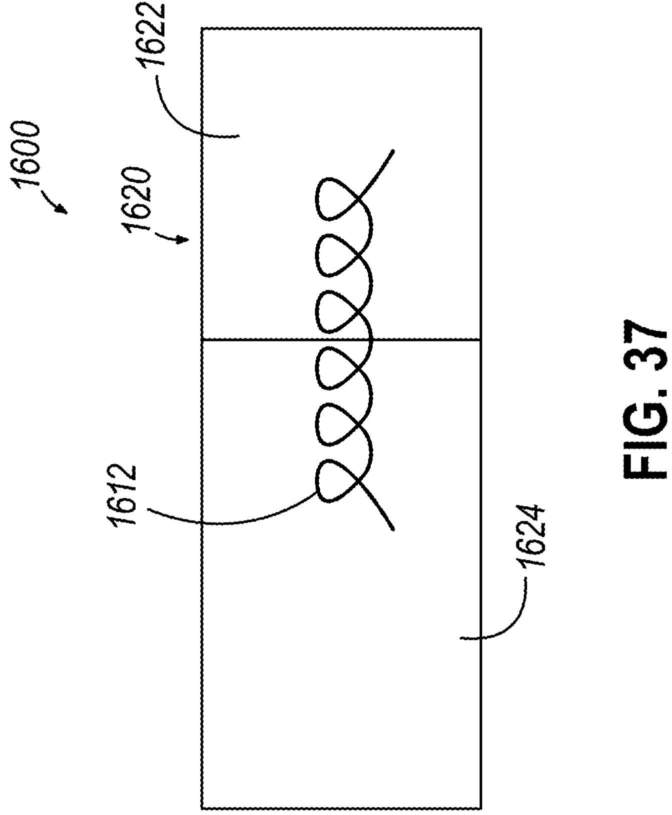
FIG. 37 depicts a side elevational view of still another exemplary biopsy site marker.

FIG. 37 shows an exemplary marker (1600) that is generally configured to rapidly expand into a predetermined shape to thereby anchor marker (1600) within tissue. Unless otherwise explicitly noted herein, marker (1600) is substantially similar to marker (100) described above. For instance, like with marker (100), marker (1600) of the present example includes a marker element (1612) and a carrier (1620). Marker element (1612) of the present example is shown as being formed as an elongate helical wire. As will be described in greater detail below, marker element (1612) is generally configured to hold various portions of marker (1600) together while providing high visibility under an imaging guidance means such as ultrasound, x-ray, MRI, and/or etc. Although marker element (1612) of the present example is shown as having a specific shape, it should be understood that other suitable shapes may be used. For instance, in some examples, marker element (1612) can be substantially similar to marker element (12) described above. In addition, marker element (1612) can be generally configured as non-bioabsorbable and radiopaque and/or echogenic to enhance visualization over time. Similarly, marker element (1612) can comprise a variety of materials such as metal, hard plastic, and/or etc.

As with carrier (120) described above, carrier (1620) of the present example is configured for absorption into a patient after placement of marker (1600). However, unlike carrier (120), carrier (1620) of the present example includes multiple marker materials (1622, 1624). Marker materials (1622, 1624) of the present examples are generally configured to have varying material properties that effect the expansion thereof such that marker (1600) can rapidly transition from an initial shape to a predetermined shape.

Marker materials (1622, 1624) are generally positioned in an axially layered arrangement. For instance, both marker materials (1622, 1624) form a cylindrical shape when in a dehydrated condition. Thus, marker (1600) generally defines an elongate cylindrical configuration. Marker materials (1622, 1624) include a plug marker material (1622) and a core marker material (1624). Plug marker material (1622) and core marker material (1624) together define the shape of carrier (1620) by being stacked in an end-to-end configuration along the longitudinal axis defined by marker (1600). In the present configuration, plug marker material (1622) is isolated to a single end of core marker material (1624). However, it should be understood that in other examples, plug marker material (1622) can be on both ends of core marker material (1624).

It should be understood that marker materials (1622, 1624) can use a variety of materials having different responses to moisture within tissue. For instance, in the present example plug marker material (1622) includes collagen, while core marker material (1624) includes hydrogel. As described above with respect to marker (500), collagen and hydrogel generally exhibit different physical responses in the presence of moisture. For instance, collagen is generally more prone to rapid absorption of moisture, thereby providing rapid expansion. Meanwhile, hydrogel absorbs moisture at a slower rate, thereby providing slower expansion. As will be described in greater detail below, these different properties can be used to influence the particular way in which marker (1600) expands after being placed within tissue. Although certain specific materials are described herein that lead to this effect, it should be understood that various alternative materials or combinations of materials can be used as will be apparent to those of ordinary skill in the art to provide the same effect.

Marker element (1612) of the present example is generally centered within plug marker material (1622) and core marker material (1624). This central configuration can be desirable so that marker element (1612) remains centered or otherwise in position within a biopsy site as marker materials (1622, 1624) degrade or absorb into tissue. Marker element (1612) also extends between plug marker material (1622) and core marker material (1624). Marker element (1612) extending between plug marker material (1622) and core marker material (1624) is generally desirable to hold or otherwise couple marker materials (1622, 1624) together. In particular, the generally helical shape of marker element (1612) fixes marker element (1612) within each marker material (1622, 1624). The extension of marker element (1612) between each marker material (1622, 1624) then holds marker materials (1622, 1624) together by virtue of the fixation of marker element (1612) within each marker material (1622, 1624).

Although marker element (1612) is shown as having a particular position within marker materials (1622, 1624), it should be understood that various alternative positions can be used. For instance, in some examples, one or more marker elements (1312) can be placed in a variety of positions either centered between plug marker material (1622) and core marker material (1624) or offset towards either plug marker material (1622) or core marker material (1624).

In use, marker (1600) can be deployed at a biopsy site. Once deployed, marker (1600) can absorb moisture within marker materials (1622, 1624). Moisture absorption can cause marker (1600) to transition to an initially hydrated state. In this state, plug marker material (1622) absorbs moisture rapidly and thereby exhibits rapid volumetric expansion. Meanwhile, core marker material (1624) absorbs moisture relatively slowly and thereby exhibits minimal volumetric expansion. These expansion properties, together with the relative positioning of plug marker material (1624) and core marker material (1622), result in marker (1600) rapidly expanding to form a predetermined shape.

The expansion properties described above result in a generally pie or mushroom-shaped profile of marker (1600) when in the initially hydrated shape. In particular, plug marker material (1622) can rapidly expand in shape to a relatively large diameter to thereby occupy a relatively large volume. Meanwhile, core marker material (1624) can undergo a relatively minimal expansion to maintain a relatively small diameter. In this configuration, plug marker material (1622) can act as a plug to prevent marker (1600) from following the passage created by the biopsy needle. Thus, the rapid expansion of plug marker material (1622) can act to hold marker (1600) within the biopsy cavity and at the biopsy site.

It should be understood that the particular shape of marker (1600) can also change throughout the course of hydration. For instance, marker (1600) can start in the initially hydrated state described above. As hydration completes, the profile shape of marker (1600) can become less prominent over time as core marker material (1624) hydrates, tissue surrounds marker (1600), and/or marker materials (1622, 1624) begin to absorb/degrade.

IV. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A biopsy site marker, comprising: a carrier and a marker element disposed within the carrier, wherein the carrier includes a first marker material and a second marker material, wherein the first marker material and the second marker material are each configured to expand in the presence of moisture, wherein the first marker material is configured to expand at a rapid rate relative to the second marker material in the presence of moisture.

Example 2

The marker of Example 1, wherein the first marker material is formed as an outer shell that encloses the second marker material.

Example 3

The marker of Example 1, wherein the first marker material includes a first portion disposed on a proximal end of the second marker material and a second portion disposed on a distal end of the second marker material.

Example 4

The marker of Example 3, wherein the first portion and the second portion of the first marker material each include one or more notches configured to receive tissue.

Example 5

The marker of Examples 3 or 4, wherein the first portion and the second portion of the first marker material are each configured to rapidly expand in the presence of moisture relative to the second marker material to form a dumbbell-shaped profile.

Example 6

The marker of Example 1, wherein the first marker material defines an inner core having a center point, wherein the second marker material defines a sheath disposed proximate the center point.

Example 7

The marker of Example 6, wherein the second marker material is configured to contain expansion of the first marker material at the center point.

Example 8

The marker of Example 1, wherein the first marker material is formed as an outer shell that encloses the second marker material, wherein the second marker material is offset within the first marker material relative to a central axis of the marker.

Example 10

The marker of Example 1, wherein the first marker material and the second marker material are connected in an end-to-end configuration.

Example 11

The marker of Example 10, wherein the first marker material is configured to expand at a rapid rate relative to the second marker material in the presence of moisture to thereby form a tissue plug.

Example 12

The marker of Example 1, wherein the second marker material defines an indentation, wherein the first marker material is disposed within the indentation of the second marker material.

Example 13

The marker of Example 12, wherein the first marker material is configured to expand at a rapid rate relative to the second marker material in the presence of moisture such that the first marker material expands out of the indentation defined by the second marker material.

Example 14

The marker of any one or more of Examples 1 through 13, wherein the first marker material is collagen, wherein the second marker material is hydrogel.

Example 15

The marker of any one or more of Examples 1 through 14, wherein the marker element is disposed within the first marker material.

Example 16

The marker of any one or more of Examples 1 through 14, wherein the marker element is disposed within the second marker material.

Example 17

The marker of any one or more of Examples 1 through 14, wherein the marker element is disposed within both the first marker material and the second marker material such that the marker element is configured to couple the first marker material to the second marker material.

Example 18

A method of manufacturing a biopsy site marker, wherein the method comprises: forming a body of a first marker material, wherein formation of the body includes forming a void extending through the body; forming a pellet of a second marker material; inserting the pellet into the void of the body; and compressing the combination of the body and the pellet.

Example 19

The method of Example 18, wherein the step of forming the pellet includes forming a plurality of pellets, wherein the step of inserting the pellet into the void of the body includes inserting the plurality of pellets into the void.

Example 20

The method of Example 18 or 20, wherein the first marker material includes a collagen, wherein the second marker material includes a hydrogel.

Example 21

A biopsy site marker, comprising: a carrier and a marker element disposed within the carrier, wherein the carrier includes a first marker material and a second marker material, wherein the first marker material defines an outer shell wrapped around a core defined by the second marker material, wherein the first marker material and the second marker material are each configured to expand in the presence of moisture, wherein the first marker material is configured to expand at a rapid rate relative to the second marker material in the presence of moisture.

Example 22

The marker of Example 21, wherein the outer shell of the first marker material entirely surrounds the core of the second marker material.

Example 23

The marker of Example 21 or 22, wherein the second marker material is configured to remain stable relative to the first marker material when exposed to moisture.

Example 24

The marker of any one or more of Examples 21 through 23, wherein the marker element is centered within the second marker material.

Example 25

The marker of any one or more of Examples 21 through 24, wherein the first marker material is configured to expand in volume by at least 300 percent when exposed to moisture.

Example 26

The marker of any one or more of Examples 21 through 25, wherein the first marker material is configured to degrade more rapidly when exposed to moisture relative to the second marker material.

Example 27

A biopsy site marker, comprising: a carrier and a marker element disposed within the carrier, wherein the carrier includes first portion, a second portion, and third portion disposed between the first portion and the second portion, wherein the first portion and the second portion both include a first marker material, wherein the third portion includes a second marker material, wherein the first marker material is configured to expand at a rapid rate relative to the second marker material in the presence of moisture.

Example 28

The marker of Example 27, wherein the first portion and the second portion each include a plurality of notches.

Example 29

The marker of Examples 27 or 28, wherein the first portion and the second portion are both configured to expand relative to the third portion to anchor the carrier within tissue.

Example 30

The marker of any one or more of Examples 27 through 29, wherein the carrier is configured to transition between a dehydrated configuration to an initially hydrated configuration, wherein the first marker material is configured to expand relative to the second marker material during the transition to the initially hydrated configuration such that the carrier forms a dumbbell-shaped profile.

Example 31

A biopsy site marker, comprising: a carrier and a marker element disposed within the carrier, wherein the carrier includes a first marker material and a second marker material, wherein the first marker material defines a cylindrical core, wherein the second marker material defines an outer sleeve surrounding a portion of the first marker material, wherein the first marker material is configured to expand at a rapid rate relative to the second marker material in the presence of moisture.

Example 32

The marker of Example 31, wherein the first marker material defines a longitudinal axis, wherein the second marker material is positioned at the center of the longitudinal axis.

Example 33

The marker of Examples 31 or 32, wherein at least a portion of the first marker material is exposed relative to the second marker material.

Example 34

The marker of any one or more of Examples 31 through 33, wherein the second marker material is configured to restrict expansion of at least a portion of the first marker material.

Example 35

The marker of any one or more of Examples 31 through 34, wherein the first marker material is collagen, wherein the second marker material is hydrogel.

Example 36

The marker of any one or more of Examples 31 through 35, wherein the marker element is positioned within the first marker material.

Example 37

The marker of any one or more of Examples 31 through 35, wherein the marker element is positioned within the second marker material.

Example 38

The marker of any one or more of Examples 31 through 35, wherein the marker element is positioned within both the first marker material and the second marker material.

Example 39

The marker of any one or more of Examples 31 through 35, wherein the marker element includes a plurality of marker elements, wherein at least one marker element is positioned in the first marker material, the second marker material, or both.

Example 40

A method for deploying a marker in a fixed location within tissue, the method comprising: positioning a biopsy site marker at a biopsy site; and permitting a first marker material and a second marker material of the biopsy site marker to expand while at the biopsy site such that the first marker material expands more rapidly relative to a second marker material of the biopsy site marker.

Example 41

The method of Example 40, further comprising relocating the biopsy site after a biopsy procedure by identifying the second marker material under an imaging guidance means.

V. CONCLUSION

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A biopsy site marker, comprising:

(a) a carrier;

(b) a marker element, wherein the carrier includes a first portion, a second portion, and a third portion, the third portion being disposed between the first portion and the second portion, wherein the first portion and the second portion both include a first marker material and are separate from one another, wherein the third portion includes a second marker material, wherein the first marker material is configured to expand at a rapid rate relative to the second marker material in a presence of moisture, wherein the marker element is disposed within the third portion, wherein each of the first portion, the second portion, and the third portion is configured to expanded to an expanded configuration when in the presence of moisture, wherein each of the first portion and the second portion include a larger circumference than the third portion when each of the first portion, the second portion, and the third portion are in the expanded configuration; and (c) a marker material interface including a first marker material interface and a second marker material interface, wherein the first marker material interface is disposed between the first portion and the third portion, and wherein the second marker material interface is disposed between the second portion and the third portion, the marker material interface coupling the first portion and the second portion to the third portion respectively, the marker material interface being configured to locally restrict expansion of an interior side of each of the first portion and the second portion, respectively.

2. The marker of claim 1, wherein the first portion and the second portion each includes a plurality of notches.

3. The marker of claim 1, wherein the first portion and the second portion are both configured to expand relative to the third portion to anchor the carrier within a tissue.

4. The marker of claim 1, wherein the carrier is configured to transition between a dehydrated configuration to an initially hydrated configuration, wherein the first marker material is configured to expand relative to the second marker material during the transition to the initially hydrated configuration such that the carrier forms a dumbbell-shaped profile.

5. The marker of claim 1, the first portion and the second portion defining a cylindrical shape, the cylindrical shape being interrupted by a plurality of axially extending notches, each notch of the plurality of notches being configured to grip a tissue.

6. The marker of claim 1, the first marker material being configured to rapidly absorb moisture relative to the second marker material.

7. The marker of claim 6, the first marker material including collagen, and the second marker material including hydrogel.

8. The marker of claim 1, the first portion, the second portion, and the third portion being arranged axially, and the first portion, the second portion, and the third portion together defining a cylindrical shape when in a dehydrated condition.

9. The marker of claim 1, the marker element being centered within the third portion.

10. The marker of claim 1, the marker element being centered both laterally and axially within the third portion.

11. The marker of claim 1, an exterior side of the first portion and an exterior side of the second portion, wherein each exterior side is configured to expand relative to the marker material interface.

12. The marker of claim 1, the first marker material including collagen, the second marker material including hydrogel, and the marker element being disposed in the hydrogel.

13. The marker of claim 1, the first marker material including collagen, the second marker material including hydrogel, and the marker element being disposed entirely in the hydrogel.

14. The marker of claim 1, the first marker material including collagen, the second marker material including hydrogel, the marker element being disposed within both a portion of the hydrogel and a portion of the collagen.

15. A biopsy site marker, comprising:

(a) a carrier, the carrier including:

(i) an inner carrier portion defining a proximal end and a distal end, (ii) a pair of outer carrier portions, each outer carrier portion being disposed on the proximal end and the distal end of the inner carrier portion, respectively, (iii) a first interface disposed between the proximal end of the inner carrier portion and the corresponding outer carrier portion, and (iv) a second interface disposed between the distal end of the inner carrier portion and the corresponding outer carrier portion; and (b) a marker element extending from the inner carrier portion to at least one of the outer carrier portions, the pair of outer carrier portions both including a first marker material, wherein the first marker material of each outer carrier portion extends continuously from corresponding first and second interfaces to respective terminal ends of the carrier, the inner carrier portion including a second marker material extending from the proximal end to the distal end, wherein the marker element is disposed in the second marker material, the first marker material being configured to expand at a rapid rate relative to the second marker material in a presence of moisture; and the first interface and the second interface both being configured to restrict a diameter of each outer carrier portion near the first interface and the second interface, respectively.

16. The marker of claim 15, the first interface and the second interface both being configured to restrict a diameter of each outer carrier portion near the first interface and the second interface, respectively, to correspond to a diameter defined by the inner carrier portion.

17. The marker of claim 15, each outer carrier portion defining a respective outer end, each outer end being configured to flare outwardly relative to the first interface and the second interface, respectively, in the presence of moisture.

18. The marker of claim 15, the marker element being disposed within the inner carrier portion.

19. A biopsy site marker, comprising:

(a) a carrier defining a proximal-most end and a distal-most end, the carrier including:

(i) an inner carrier portion defining a proximal end and a distal end, (ii) a proximal outer carrier portion, (iii) a distal outer carrier portion, the distal outer carrier portion and the proximal outer carrier portion being disposed on the distal end and the proximal end of the inner carrier portion, respectively, (iv) a first interface disposed between the proximal end of the inner carrier portion and the proximal outer carrier portion, and (v) a second interface disposed between the distal end of the inner carrier portion and the distal outer carrier portion; and (b) a marker element disposed within the carrier, the proximal outer carrier portion including a first marker material extending from the proximal-most end to the first interface and the distal outer carrier portion including the first marker material extending from the distal-most end to the second interface, the inner carrier portion including a second marker material extending from the first interface to the second interface, the first marker material being configured to expand at a rapid rate relative to the second marker material in a presence of moisture; and the first interface and the second interface both being configured to locally restrict a size of the proximal outer carrier portion and the distal outer carrier portion near the first interface and the second interface, respectively.

* * * * *